(12) United States Patent
Olson et al.

(10) Patent No.: US 11,633,546 B2
(45) Date of Patent: Apr. 25, 2023

(54) PALM ACTIVATED DRUG DELIVERY DEVICE

(71) Applicant: Janssen Biotech, Inc., Malvern, PA (US)

(72) Inventors: Lorin P. Olson, Scotts Valley, CA (US); Peter Krulevitch, Pleasanton, CA (US); James Glencross, Edinburgh (GB); Jingli Wang, San Jose, CA (US); Nicholas Foley, Edinburgh (GB); Mingqi Zhao, San Jose, CA (US)

(73) Assignee: Janssen Biotech, Inc., Malvern, PA (US)

( * ) Notice: Subject to any disclaimer, the term of this patent is extended or adjusted under 35 U.S.C. 154(b) by 755 days.

(21) Appl. No.: 16/663,610

(22) Filed: Oct. 25, 2019

(65) Prior Publication Data

US 2020/0054838 A1    Feb. 20, 2020

Related U.S. Application Data

(62) Division of application No. 14/939,416, filed on Nov. 12, 2015, now Pat. No. 10,485,931, which is a
(Continued)

(51) Int. Cl.
*A61M 5/32* (2006.01)
*A61M 5/31* (2006.01)
(Continued)

(52) U.S. Cl.
CPC ........ *A61M 5/3202* (2013.01); *A61M 5/2033* (2013.01); *A61M 5/315* (2013.01);
(Continued)

(58) Field of Classification Search
CPC .... A61M 2005/2026; A61M 2005/208; A61M 2005/3126; A61M 2005/3247;
(Continued)

(56) References Cited

U.S. PATENT DOCUMENTS 3,742,948 A    7/1973   Post et al.
D323,032 S     1/1992   McCrary
(Continued)

FOREIGN PATENT DOCUMENTS

CA    2465122 A1    12/2003
CA    2595730 A1    7/2006
(Continued)

OTHER PUBLICATIONS

"Self-Injection Technologies Self Dose Injector Platform Technology", West Pharmaceutical Inc., https://web.archive.org/web/20121016052111/http://www.westpharma.com/en/p- roducts/pages/selfdose.aspx, Oct. 16, 2012, 1 page.
(Continued)

*Primary Examiner* — Rebecca E Eisenberg
(74) *Attorney, Agent, or Firm* — BakerHostetler

(57) ABSTRACT

Disclosed is a device for the parenteral delivery of a medication, such as a drug. The device includes upper and lower housings in which the upper housing is configured to move relative to the lower housing as a result of application of an external force to permit the user of the device to control the rate at which the drug is administered.

20 Claims, 21 Drawing Sheets

Related U.S. Application Data division of application No. 12/905,572, filed on Oct. 15, 2010, now Pat. No. 9,216,256.

(60) Provisional application No. 61/361,983, filed on Jul. 7, 2010, provisional application No. 61/252,378, filed on Oct. 16, 2009.

(51) Int. Cl.
A61M 5/315 (2006.01)
A61M 5/50 (2006.01)
A61M 5/20 (2006.01)

(52) U.S. Cl.
CPC ...... A61M 5/3129 (2013.01); A61M 5/31501 (2013.01); A61M 5/31511 (2013.01); A61M 5/326 (2013.01); A61M 5/3243 (2013.01); A61M 5/3287 (2013.01); A61M 5/50 (2013.01); A61M 5/20 (2013.01); A61M 5/2046 (2013.01); A61M 5/2053 (2013.01); A61M 5/3157 (2013.01); A61M 5/321 (2013.01); A61M 5/3204 (2013.01); A61M 5/5086 (2013.01); A61M 2005/208 (2013.01); A61M 2005/2026 (2013.01); A61M 2005/3123 (2013.01); A61M 2005/3125 (2013.01); A61M 2005/3126 (2013.01); A61M 2005/3247 (2013.01); A61M 2205/581 (2013.01); A61M 2205/582 (2013.01); A61M 2205/583 (2013.01); A61M 2205/584 (2013.01); A61M 2205/586 (2013.01)

(58) Field of Classification Search
CPC .............. A61M 2205/581; A61M 5/20; A61M 5/2033; A61M 5/31511; A61M 5/50
See application file for complete search history.

(56) References Cited

U.S. PATENT DOCUMENTS

| | | |
|---|---|---|
| 5,271,527 A | 12/1993 | Haber et al. |
| 5,295,965 A | 3/1994 | Wilmot |
| 5,378,233 A | 1/1995 | Haber et al. |
| 5,540,664 A | 7/1996 | Wyrick |
| 5,688,241 A | 11/1997 | Asbaghi |
| 5,795,336 A | 8/1998 | Romano et al. |
| 5,873,856 A | 2/1999 | Hjertman et al. |
| 5,938,642 A | 8/1999 | Burroughs et al. |
| 5,957,896 A | 9/1999 | Bendek et al. |
| D418,917 S | 1/2000 | Duchon et al. |
| D428,650 S | 7/2000 | Bellhouse et al. |
| 6,183,446 B1 | 2/2001 | Jeanbourquin |
| 6,221,046 B1 | 4/2001 | Burroughs et al. |
| 6,235,004 B1 | 5/2001 | Steenfeldt-Jensen et al. |
| 6,547,764 B2 | 8/2003 | Gullak et al. |
| 6,602,222 B1 | 8/2003 | Roser |
| D485,365 S | 1/2004 | Py et al. |
| D488,382 S | 4/2004 | Calello |
| 6,726,657 B1 | 4/2004 | Dedig et al. |
| D491,275 S | 6/2004 | Walters et al. |
| 6,743,205 B2 | 6/2004 | Nolan et al. |
| 6,805,686 B1 | 10/2004 | Fathallah et al. |
| 6,808,507 B2 | 10/2004 | Roser |
| D510,139 S | 9/2005 | Gilad et al. |
| 6,986,760 B2 | 1/2006 | Giambattista et al. |
| 7,011,649 B2 | 3/2006 | De et al. |
| 7,074,211 B1 | 7/2006 | Heiniger et al. |
| 7,112,187 B2 | 9/2006 | Karlsson |
| D533,457 S | 12/2006 | Snyder |
| D548,336 S | 8/2007 | Galbraith |
| 7,252,651 B2 | 8/2007 | Haider et al. |
| D559,396 S | 1/2008 | Dave |
| 7,314,464 B2 | 1/2008 | Dickinson |
| D562,987 S | 2/2008 | Colin et al. |
| D567,388 S | 4/2008 | Harold et al. |
| 7,361,160 B2 | 4/2008 | Hommann et al. |
| D577,814 S | 9/2008 | Seki et al. |
| D596,744 S | 7/2009 | Hull et al. |
| 7,585,287 B2 | 9/2009 | Bresina et al. |
| D612,487 S | 3/2010 | Hunter et al. |
| D613,400 S | 4/2010 | Hunter et al. |
| D613,401 S | 4/2010 | Hunter et al. |
| D613,861 S | 4/2010 | Hunter et al. |
| 7,744,565 B2 | 6/2010 | Heiniger et al. |
| D619,720 S | 7/2010 | Cheetham |
| D623,738 S | 9/2010 | Van Der Stappen |
| D627,459 S | 11/2010 | Uchida et al. |
| D633,199 S | 2/2011 | Mackay et al. |
| 7,918,824 B2 | 4/2011 | Bishop et al. |
| D644,516 S | 9/2011 | Howell et al. |
| D644,529 S | 9/2011 | Padain et al. |
| D647,613 S | 10/2011 | Paget et al. |
| D677,382 S | 3/2013 | Foley et al. |
| D678,514 S | 3/2013 | Foley et al. |
| D697,205 S | 1/2014 | Schneider et al. |
| D719,650 S | 12/2014 | Arinobe et al. |
| 9,216,256 B2 | 12/2015 | Olson et al. |
| 9,233,213 B2 | 1/2016 | Olson et al. |
| 9,352,099 B2 | 5/2016 | Roberts et al. |
| 10,485,931 B2 | 11/2019 | Olson et al. |
| 10,500,348 B2 | 12/2019 | Olson et al. |
| 10,646,662 B2 | 5/2020 | Sadowski et al. |
| 10,796,604 B2 | 10/2020 | Edwards et al. |
| 2002/0004648 A1 | 1/2002 | Larsen et al. |
| 2003/0014018 A1 | 1/2003 | Giambattista et al. |
| 2003/0014019 A1 | 1/2003 | Saied |
| 2003/0105430 A1 | 6/2003 | Lavi et al. |
| 2003/0229314 A1 | 12/2003 | Mcwethy et al. |
| 2004/0019326 A1 | 1/2004 | Gilbert et al. |
| 2005/0010136 A1 | 1/2005 | Restelli et al. |
| 2005/0027255 A1 | 2/2005 | Lavi et al. |
| 2005/0085839 A1 | 4/2005 | Allen et al. |
| 2005/0096599 A1 | 5/2005 | Crawford et al. |
| 2005/0222539 A1 | 10/2005 | Gonzales et al. |
| 2005/0273061 A1 | 12/2005 | Hommann et al. |
| 2006/0142691 A1 | 6/2006 | Trautman et al. |
| 2006/0189938 A1 | 8/2006 | Hommann et al. |
| 2006/0229569 A1 | 10/2006 | Lavi et al. |
| 2006/0270984 A1 | 11/2006 | Hommann |
| 2006/0270985 A1 | 11/2006 | Hommann et al. |
| 2006/0276756 A1 | 12/2006 | Francavilla |
| 2007/0016142 A1 | 1/2007 | Burren et al. |
| 2007/0135767 A1 | 6/2007 | Gillespie et al. |
| 2007/0173770 A1 | 7/2007 | Stamp |
| 2008/0154200 A1 | 6/2008 | Lesch |
| 2008/0228147 A1 | 9/2008 | David-Hegerich et al. |
| 2008/0269692 A1 | 10/2008 | James et al. |
| 2009/0024093 A1 | 1/2009 | Carrel et al. |
| 2009/0292257 A1 | 11/2009 | Barrelle et al. |
| 2009/0299288 A1 | 12/2009 | Sie et al. |
| 2009/0299295 A1 | 12/2009 | Rubinstein et al. |
| 2009/0318864 A1 | 12/2009 | Carrel et al. |
| 2010/0152655 A1 | 6/2010 | Stamp |
| 2010/0292653 A1 | 11/2010 | Maritan |
| 2011/0092915 A1 | 4/2011 | Olson et al. |
| 2011/0245770 A1 | 10/2011 | Carrel et al. |
| 2013/0204195 A1 | 8/2013 | Ekman et al. |
| 2013/0204229 A1 | 8/2013 | Olson et al. |
| 2013/0226085 A1 | 8/2013 | Roberts et al. |
| 2013/0331796 A1 | 12/2013 | Wozencroft |
| 2014/0303564 A1 | 10/2014 | Roberts |
| 2016/0058955 A1 | 3/2016 | Olson et al. |
| 2016/0089503 A1 | 3/2016 | Olson et al. |

FOREIGN PATENT DOCUMENTS

| | | |
|---|---|---|
| CA | 2905774 A1 | 11/2007 |
| CN | 88101171 A | 9/1988 |
| CN | 1471414 A | 1/2004 |
| CN | 101132820 A | 2/2008 |
| CN | 101346157 A | 1/2009 |
| CN | 101879342 A | 11/2010 |
| CN | 102137691 A | 7/2011 |

(56) References Cited

FOREIGN PATENT DOCUMENTS

| | | |
|---|---|---|
| CN | 102149420 A | 8/2011 |
| CN | 102264418 A | 11/2011 |
| CN | 102665805 A | 9/2012 |
| DE | 2137405 A1 | 2/1973 |
| EP | 1362609 A1 | 11/2003 |
| EP | 1410818 A1 | 4/2004 |
| EP | 1483004 B1 | 12/2004 |
| EP | 1621222 A1 | 2/2006 |
| EP | 1703929 A1 | 9/2006 |
| EP | 1849448 A1 | 10/2007 |
| EP | 1888149 | 2/2008 |
| EP | 2488237 A2 | 8/2012 |
| EP | 2588166 A1 | 5/2013 |
| EP | 2588167 A1 | 5/2013 |
| EP | 2588168 B1 | 5/2013 |
| EP | 2646101 A4 | 10/2013 |
| EP | 2654854 A2 | 10/2013 |
| EP | 2661293 A1 | 11/2013 |
| EP | 2667914 A1 | 12/2013 |
| EP | 2667915 A1 | 12/2013 |
| EP | 2694141 A1 | 2/2014 |
| EP | 2907537 A1 | 8/2015 |
| EP | 3235530 A1 | 10/2017 |
| FR | 2770404 A1 | 5/1999 |
| FR | 2884722 A1 | 10/2006 |
| FR | 2905273 A1 | 3/2008 |
| JP | 05-245197 A | 9/1993 |
| JP | 07-136263 A | 5/1995 |
| JP | 2005-530565 | 10/2005 |
| JP | 2007-500530 A | 1/2007 |
| JP | 2007-117438 A | 5/2007 |
| JP | 2008-220949 A | 9/2008 |
| JP | 2008-536597 | 9/2008 |
| JP | 2009-060982 A | 3/2009 |
| JP | 2009-523587 A | 6/2009 |
| JP | 2009-534072 A | 9/2009 |
| JP | 4785831 B2 | 10/2011 |
| JP | 1431935 S | 1/2012 |
| JP | 2013-508032 | 3/2013 |
| JP | 2013-520214 A | 6/2013 |
| KR | 10-2004-0103930 A | 12/2004 |
| KR | 10-2006-0129024 A | 12/2006 |
| KR | 10-2009-0025305 A | 3/2009 |
| KR | 10-2012-0095386 A | 8/2012 |
| KR | 2013-0012967 A | 2/2013 |
| KR | 10-2020-0104434 A | 9/2020 |
| MX | 2007009152 | 3/2008 |
| MX | 2012004446 A | 6/2012 |
| RU | 2340362 C2 | 12/2008 |
| UA | 2012/10236 | 10/2012 |
| UA | 2014/01074 | 4/2014 |
| UA | 110026 | 11/2015 |
| WO | 02/32484 A1 | 4/2002 |
| WO | 2004/000395 A1 | 12/2003 |
| WO | 2005/058396 A1 | 6/2005 |
| WO | 2005/070481 A1 | 8/2005 |
| WO | 2005/113039 A1 | 12/2005 |
| WO | 2006/079064 A1 | 7/2006 |
| WO | 2006/083876 A2 | 8/2006 |
| WO | 2006/111859 A1 | 10/2006 |
| WO | 2006/111864 A1 | 10/2006 |
| WO | 2006/117691 A1 | 11/2006 |
| WO | 2006/129196 A1 | 12/2006 |
| WO | 2008/005315 A2 | 1/2008 |
| WO | 2008/010738 A2 | 1/2008 |
| WO | 2009/095805 A2 | 8/2009 |
| WO | 2010/017650 A1 | 2/2010 |
| WO | 2010/146358 A2 | 12/2010 |
| WO | 2011/047298 A2 | 4/2011 |
| WO | 2011/101383 A1 | 8/2011 |
| WO | 2011/109205 A2 | 9/2011 |
| WO | 2012/000833 A1 | 1/2012 |
| WO | 2012/000834 A1 | 1/2012 |
| WO | 2012/000941 A2 | 1/2012 |
| WO | 2012/073035 A1 | 6/2012 |
| WO | 2012/075421 A1 | 6/2012 |
| WO | 2012/085585 A2 | 6/2012 |
| WO | 2012/093071 A1 | 7/2012 |
| WO | 2012/093075 A1 | 7/2012 |
| WO | 2012/101629 A1 | 8/2012 |
| WO | 2012/103140 A1 | 8/2012 |
| WO | 2012/138285 A1 | 10/2012 |
| WO | 2013/032779 A2 | 3/2013 |

OTHER PUBLICATIONS

FR 2884722 Machine Translation to English of the abstract and description.
International Search Report, Appln No. PCT/US2010/052894, dated Jan. 31, 2011, European Patent Office, Rijswijk, Netherlands, 4 pages.
International Search Report, Appln No. PCT/US2010/052894, dated Jun. 14, 2011, European Patent Office, Rijswijk, Netherlands, 6 pages.
U.S. Appl. filed Mar. 15, 2013, Foley et al., U.S. Appl. No. 29/449,399.
Zosano Pharma—ZP-PTH, ZP PTH—Lead Product http://www.zosanopharma.com/index.php?option=com.sub.—content&task=view&- id=127&Itemid=167, Last accessed Jun. 2, 2011.

PALM ACTIVATED DRUG DELIVERY DEVICE

CROSS-REFERENCE TO RELATED APPLICATIONS

This application is a divisional application of U.S. patent application Ser. No. 14/939,416, filed Nov. 12, 2015, which is a divisional application of U.S. patent application Ser. No. 12/905,572, filed Oct. 15, 2010, which claims priority to U.S. Provisional Application Ser. No. 61/361,983, filed Jul. 7, 2010, and U.S. Provisional Application Ser. No. 61/252,378, filed Oct. 16, 2009, the disclosures of all of which are hereby incorporated by reference as if set forth in their entirety herein.

FIELD OF THE INVENTION

The invention generally relates to methods and devices for parenteral drug delivery. The devices provide for assisted manual drug delivery with confirmation of completion of the drug delivery process. The devices provide a system with improved safety and ease of use and audible, or other forms of, feedback to the user to indicate when drug delivery is in process, completed, or both, to avoid one or both of incomplete dosing and wasted medication as well as to provide a system with improved safety and ease of use.

BACKGROUND OF THE INVENTION

For many years, an accepted method for parenteral drug delivery has been through the use of syringe and needle. The syringe contains a quantity of a drug sold either in a pre-filled syringe or introduced into a syringe by drawing the drug into a syringe from a vial or other container. Syringes have been widely accepted due to their low manufacturing cost and simple, effective design. For the user, however, syringes and needles have a number of drawbacks.

One drawback is that many patients have a fear of needles. In instances in which self-medication is required, such as those requiring multiple, daily injections, patients may not administer their medication according to their prescribed regimen due to the fear of needles, the pain that is often associated with an injection, the dexterity that is required to properly administer a drug via needle and syringe or other, similar factors. For some, that have their vision, dexterity, or awareness impaired, self-administration via needle and syringe may present additional difficulties that can prevent them from receiving their required medication.

There also are safety and disposal concerns associated with needles and syringes not only for the patient, but for those around them, that may result from contaminated needles, accidental punctures, cross-contamination, and the like, in addition to the social stigma associated with a needle and syringe drug-treatment regimen. Despite these drawbacks, however, many patients are encouraged to use needles and syringes to deliver their medication due to the ability to control insertion of the needle and the speed of the drug delivery when the plunger in the syringe is depressed and, therefore, control their perception of pain and discomfort associated with this type of drug injection.

Several advances have been made over the years to help facilitate self-administration of medication. Such advances include smaller needles with improved tip-geometry to reduce the pain. Safety syringes that encase the needle before, after, or before and after use have been used to minimize concerns over accidental punctures with needles. Improved ergonomics in syringe design, as well, have been promoted to reduce the dexterity required to accurately and safely self-administer medication via needle and syringe. Pre-filled disposable devices having a form-factor similar to that of a pen were developed to improve dosing accuracy, and auto-injectors have been used to hide the needle from the patient to reduce fears and safety concerns either by retracting the needle or placing a shield around the needle.

While such advances have improved needle and syringe based drug delivery, ergonomic designs, pens, and auto-injectors all retain a substantial similarity to the original needle and syringe concept, thus limiting their acceptance by patients who need to self-administer their medication. Current systems employ a form factor that suggests the common "grab and stab" injection technique, wherein the user grips the device in the palm and places the thumb over an activation button.

Current auto-injectors transfer control of drug delivery into the body to a mechanical system. Because such a system is highly dependent on the specific mechanical design of the auto-injector, patients may require specialized training to use the device and still risk inaccurate dosing. This situation is highly problematic when delivering very expensive drugs that might only be administered on a weekly or even more infrequent basis.

The typical method of use of current auto-injectors includes the patient holding the device against the skin for several seconds while the device is in the process of delivering medication. Many users, and the elderly in particular, may experience fatigue in their arm or hand causing them to exert uneven pressure of the device against the skin, or they may remove the device prematurely. Either situation can result in inaccurate dosing, wasted medication, increased discomfort, and the like. Under any of these circumstances, the current devices and methods that include, or evolved from, the traditional syringe and needle system have shortcomings that compromise the efficacy of a prescribed drug regimen.

Finally, as with any health-care related device or service, the cost of any frequently used component of a treatment regimen must be considered. While providing drugs in vials that are used to fill empty syringes at, or about, the time of a patient's medication may provide the least expensive solution, it adds an additional opportunity for waste or loss of an expensive drug. If that drug requires refrigeration, it may experience degradation each time it is removed and reinserted into the refrigeration device before and after filling the syringe, which can lead to less than expected drug efficacy if the vial contains a quantity of drug that is delivered over a long period of time. While pre-filled syringes offer an advantage in both reliability and convenience, such devices still have the inherent drawbacks previously recited.

With devices such as pre-filled auto-injectors, the device is most commonly manufactured for use with a wide variety of medications, but is tailored to no one medication. Because such devices rely on mechanical systems employing springs to control the injection rate of the drug, many drugs of different viscosity or that require refrigeration and change viscosity appreciably as a result of temperature change, may be delivered too quickly or too slowly for the predetermined spring-force of the auto-injector design. In many instances, too low a spring force may result in incomplete drug delivery, removal of the device before completion of the delivery, or excessive pain and discomfort to the user resulting from a prolonged period during which the injection device is inserted into the body. Too high a spring force, however, can result in drug delivery that is so rapid that it degrades the drug, or may cause injection force pain to the patient caused by rapid delivery of an acidic drug or by inducing a pressure gradient under the skin or in a vein.

Thus, there are many opportunities for advancement in the field of episodic, parenteral drug delivery that could overcome "needle-phobia", reduce pain to the patient, and increase the safety, reliability and efficacy of many drug treatment regimen.

DETAILED DESCRIPTION OF THE INVENTION AND PREFERRED EMBODIMENTS

The following detailed description is to be read with reference to the drawings in which like elements in different drawings are identically numbered. The drawings, which are not necessarily to scale, depict exemplary embodiments for the purpose of explanation only and are not intended to limit the scope of the invention. The detailed description illustrates by way of example, not by way of limitation, the principles of the invention.

The present invention is a drug delivery device, and methods for its use, which device overcomes many of the limitations and drawbacks of conventional syringes and needles as well as auto-injector-type devices. To overcome the drawbacks and limitations of prior devices and to address the unfilled needs in the art, embodiments of the presently disclosed device and methods include a device that is configured such that the user does not see and cannot touch the needle, reducing needle-phobia and potential for needle contamination. This includes automatic shielding of the needle after delivery of the drug.

Embodiments of the device have an ergonomic form-factor that permits operation one handedly and conveniently allows for alternate site injections, such as the leg, arm, or abdomen. In embodiments that include a pressure-sensitive triggering, a needle guard latch inhibits movement of the needle. In this manner, the device includes a safety mechanism that will not allow the needle to be exposed if it is not pressed against the injection site.

In FIGS. 1A-1D is illustrated one embodiment of the device of the invention that includes a window 104 to view the drug prior to use. A colored indicator may appear in the window after the device has been used, to provide a visual indication to the user of whether the device's drug has been spent. Further, after the drug is delivered, increased safety and reduction in the possibility of accidental needle punctures is provided.

Figure 4:
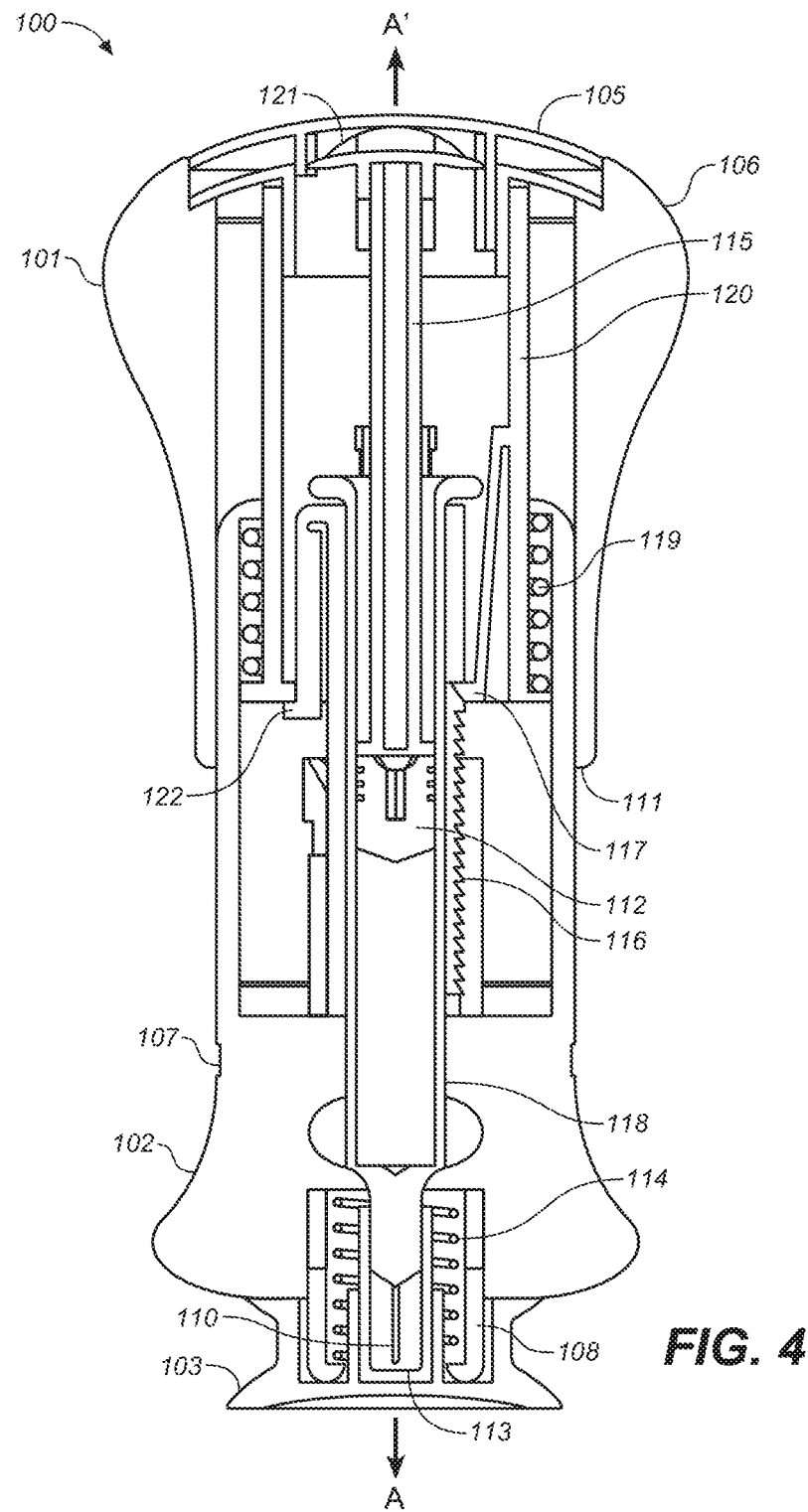
FIG. 4 is a depiction of a cross-sectional view of the embodiment of FIG. 1A.
Figure 5:
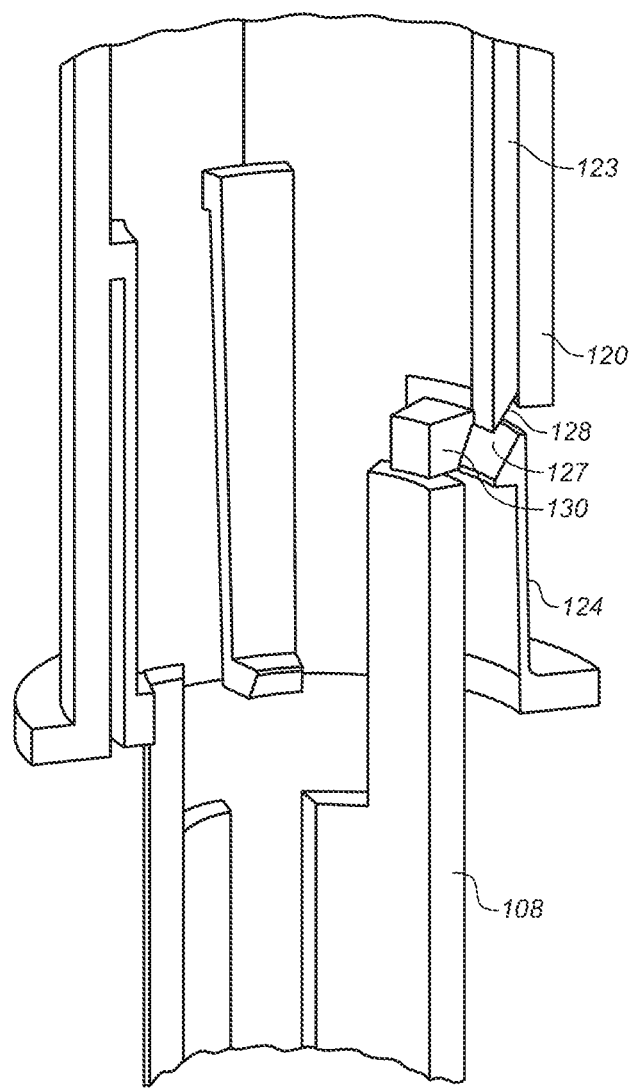
FIG. 5 is a depiction of a partial cross-sectional view of a portion of the embodiment of FIG. 1A, depicting a latch.
Figure 7:
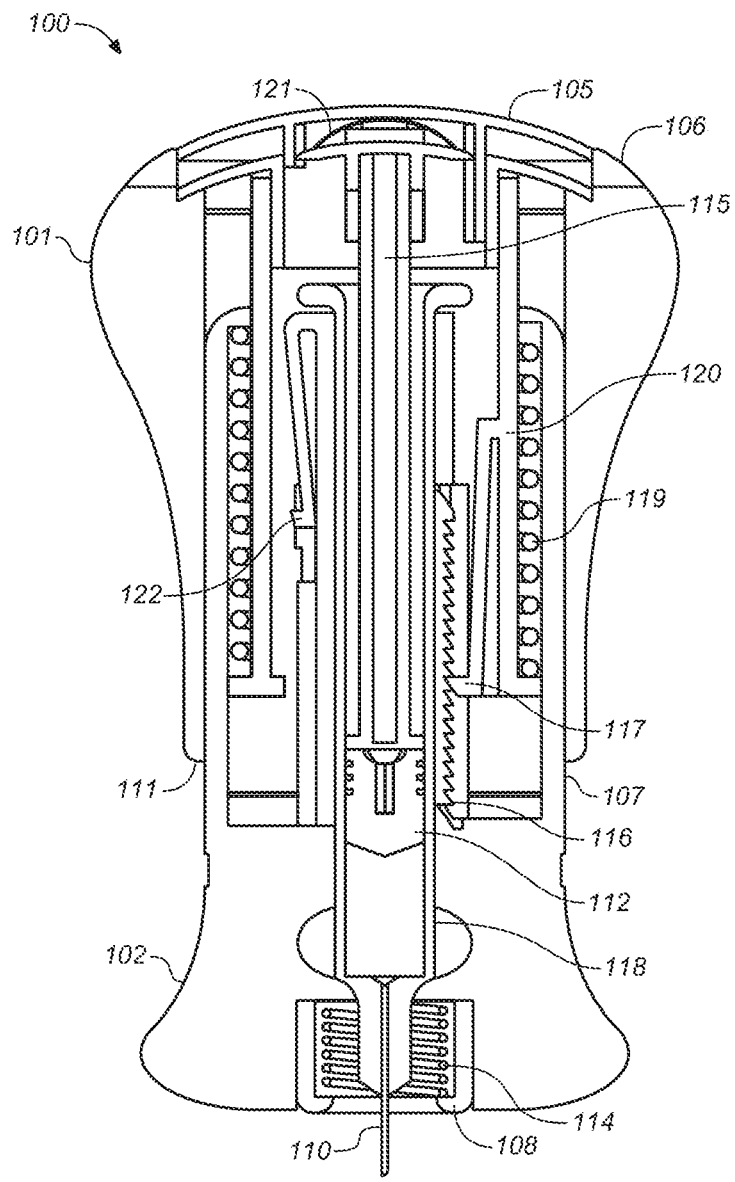
FIG. 7 is a depiction of a cross-sectional view of the embodiment of FIG. 2A.

To ensure that the user is aware of the status of the drug delivery and whether it is completed, this embodiment of the invention includes pawls and ratchets, such as those illustrated by the pawl 117 and ratchet 116 shown in FIGS. 4 and 7, that engage to produce one or more audible clicks when the injection is completed. Such a mechanism may signal the user that the dose has been delivered and the device can be removed from the skin, preventing premature withdrawal of the device from the injection site. Thus, the user actively participates during the entire delivery process, unlike conventional auto-injectors for which the user may need to wait several seconds for an assurance that the full dose has been administered.

To provide greater feedback to the user, the disclosed system of pawls and ratchets also provides audible clicks and motion of the device during delivery to indicate that the injection is progressing. In yet another embodiment, a louder click at the end of delivery alone or in combination with a visual indicator provides 1 feedback confirming that the delivery is completed.

Moreover, the present invention has a friendly, unintimidating design and method of operation, unlike conventional needle safety devices and auto-injectors, which are reminiscent of syringes and discomforting to the user. Additionally, unlike conventional auto-inserters, the user controls insertion of the needle and injection of the drug as described hereinafter.

In FIGS. 1 through 9 are shown an exemplary device of the of the invention. In FIGS. 1A through 1D is shown an embodiment of the device in various stages leading up to injection of the drug and in FIGS. 2A through 2C is shown the embodiment during and after injection of the drug. FIG. 1A shows the device 100 in its pre-use configuration as it may be received by the user. In this relaxed position, upper housing 101 partially overlies the proximal or uppermost portion of lower housing 102. In describing the various embodiments of the device, the term proximal is used in relation to the bottom surface of the device. For example, in FIG. 1B, proximal is used in relation to bottom surface or bottom 131 of device 100.

Figure 3:
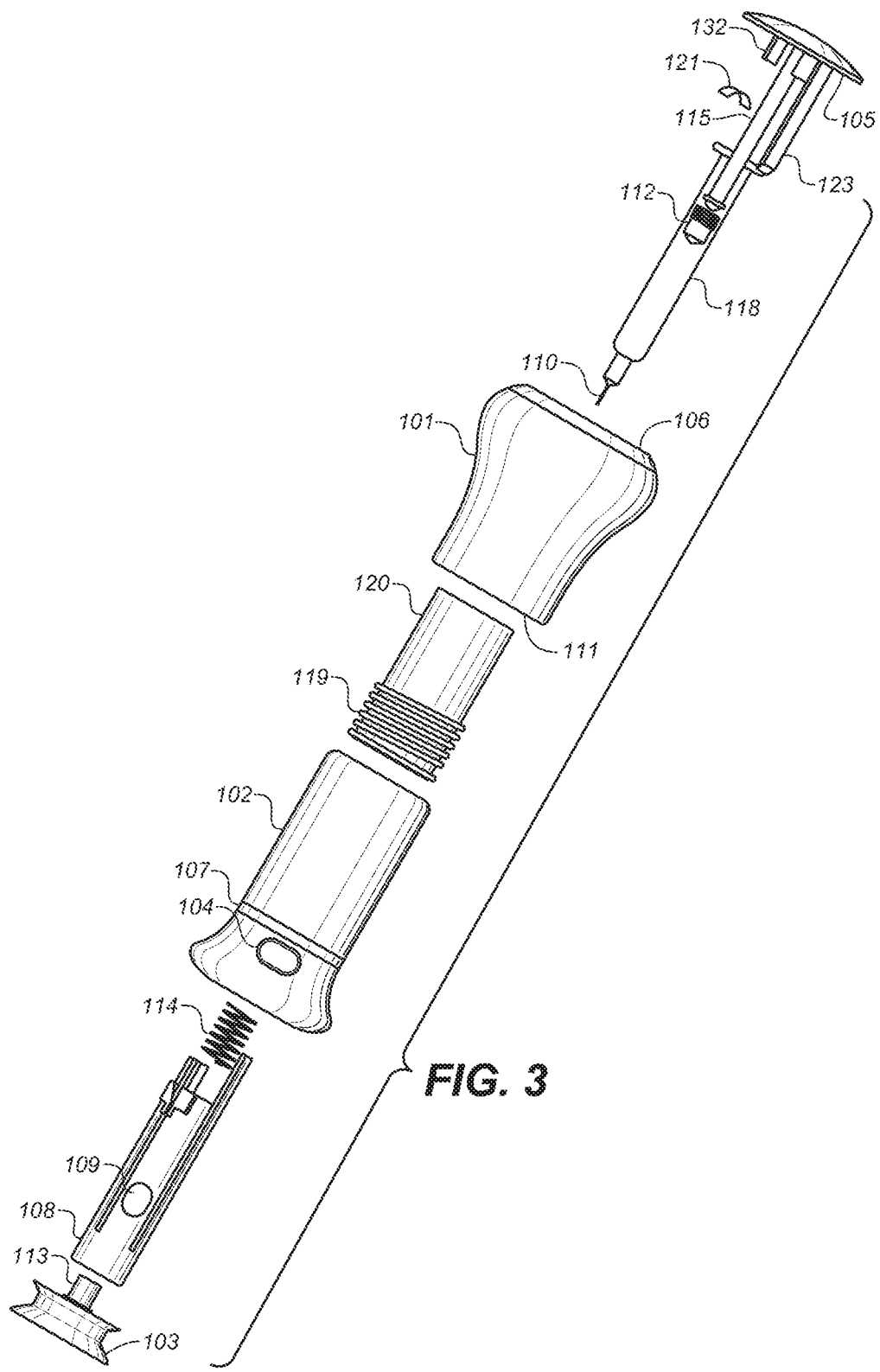
FIG. 3 is a depiction of an exploded view of the embodiment of FIG. 1A.

As shown, the device's outwardly visible features include upper housing 101, lower housing 102, cap 103, window 104, interlock button 105, grip ring 106, bottom edge 111 of the upper housing 101 and dose indicator 107. FIG. 3 is an exploded view of the components of this embodiment of the invention.

Figure 1A:
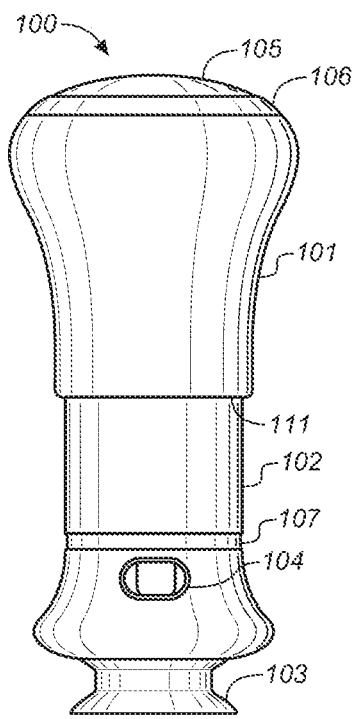
FIG. 1A is a side view of an embodiment of the present invention.
Figure 1B:
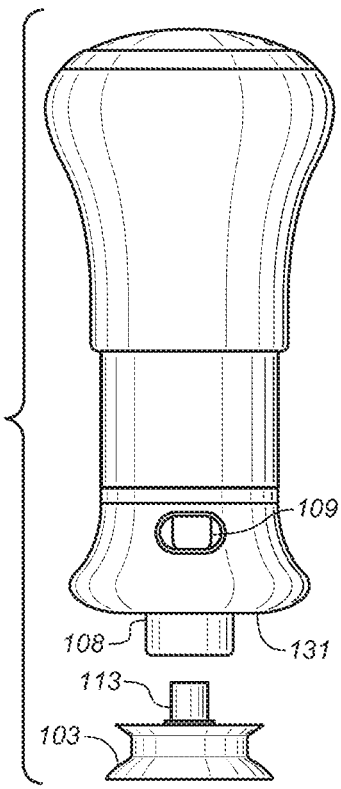
FIG. 1B is a side view of the embodiment of FIG. 1A after cap removal.

A preliminary step in using the device is to remove cap 103, which is removably attached to lower housing 102, as shown in FIG. 1B. Removing the cap 103 simultaneously removes needle shield 113 and exposes needle guard 108. Window 104 and needle guard slot 109, each of which are preferably present on both sides of the device, allow the user to view and inspect an internally housed syringe 118 and its drug contents.

In use, the device is grasped by placing the palm of the hand over the top of the upper housing 101, similar to how one grasps a floor-mounted, automotive gear shift. Grip ring 106 provides a visual cue to the user on how to grasp the device. In one embodiment, grip ring 106 is covered, or coated, or made of a suitable elastomeric material including, without limitation, neoprene rubber, urethane, polyurethane, silicone, natural rubber, thermoplastic elastomer ("TPE"), or combinations thereof to provide a non-slip and comfortable gripping surface.

Figure 1C:
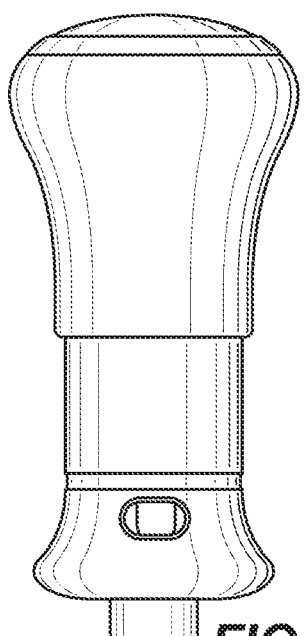
FIG. 1C is a side view of the embodiment of FIG. 1B after depression of the interlock button.
Figure 1D:
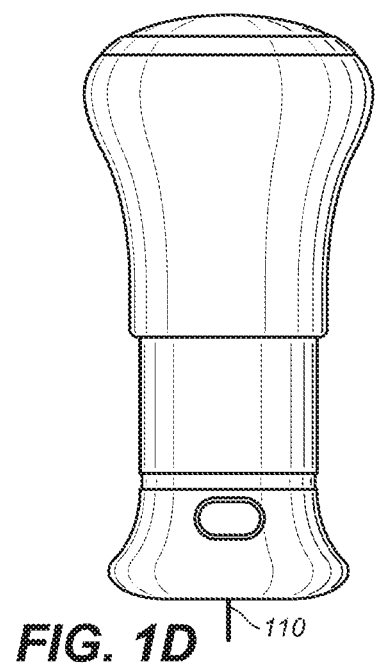
FIG. 1D is a side view of the embodiment of FIG. 1C after the needle guard has been retracted, exposing the needle.

The user presses the device, by downward pressure of the palm on grip ring 106 and interlock button 105, against the body at the desired injection location, typically the top or side of the upper leg, the abdomen, or the side or back of the upper arm. The pressure of the palm on interlock button 105 causes it to deflect downwardly, as shown in FIG. 1C, which in turn unlatches needle guard latch 124, shown in FIG. 5, allowing the needle guard 108 to slide upwardly, and exposing needle 110 (note that some device components have been removed from FIG. 5 for illustration purposes). Needle guard latch 124 is formed integrally with a portion of the distal end of upper housing sleeve 120. Upper housing sleeve 120 is a hollow cylinder a portion of which resides in the upper housing 101 and portion of which resides in lower housing 102 when the device is in the relaxed position. Upper housing sleeve 120 is fixedly attached to upper housing 101 and performs latching functions and acts to trap biasing element 119 against lower housing 102 as described in more detail below.

Needle guard latch 124 includes inwardly, with respect to the longitudinal center axis A-A' of the device, ramped surface 127 and stop 130 at its uppermost end. To unlatch the needle guard latch 124, an outwardly ramped surface 128, complementary to surface 127, that forms the distal end of interlock button extension 123, engages ramped surface 127 on the needle guard latch 124. Engagement of surfaces 127 and 128 causes the needle guard latch 124 to deflect outwardly, with respect to the center axis, removing stop 130 from blocking the upward movement of needle guard 108. The latching mechanism and needle guard 108 are preferably configured so upward movement of needle guard 108 is prevented unless the interlock button 105 is fully depressed. This protects the needle from contamination and damage due to contact with other surfaces, protects the user from accidental needle punctures, and shields the needle from view.

As the user continues to press downwardly on upper housing 101, needle guard 108 moves upwardly, exposing and allowing needle 110 to penetrate the user's skin, stopping when bottom surface 131 of the lower housing 102 is substantially flush against the skin. Once needle guard 108 passes beyond stop 130, the user may release interlock button 105, or chose not to, without affecting the remaining injection steps. When interlock button 105 is released, resilient member 121, returns interlock button 105 to the up position. Movement guide 132 acts to ensure that interlock button travels straight up and down.

The needle insertion process described herein gives control of insertion to the user. This feature allows the user to take advantage of a commonly used method often employed by insulin-dependent diabetics: if the needle is brought into contact with the skin and held there without piercing the skin, after a few seconds the user will no longer feel the presence of the needle, at which point the needle can be inserted pain free by increasing the pressure applied to the needle.

Figure 2A:
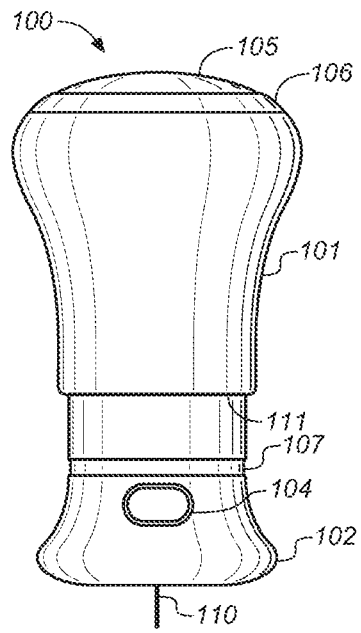
FIG. 2A is a side view of the embodiment of FIG. 1D during drug injection.
Figure 2B:
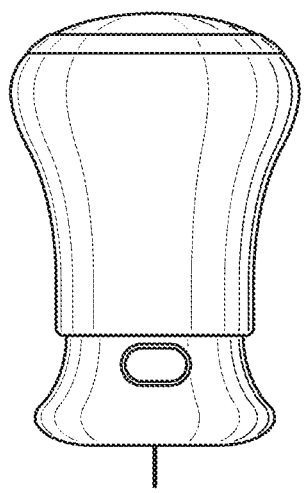
FIG. 2B is a side view of the embodiment of FIG. 2A upon completion of drug injection.
Figure 2C:
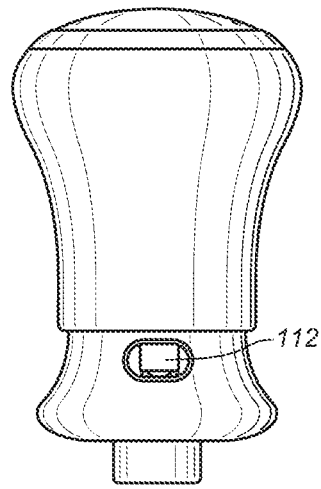
FIG. 2C is a side view of the embodiment of FIG. 2B after the needle guard has been extended, concealing the needle.
Figure 6:
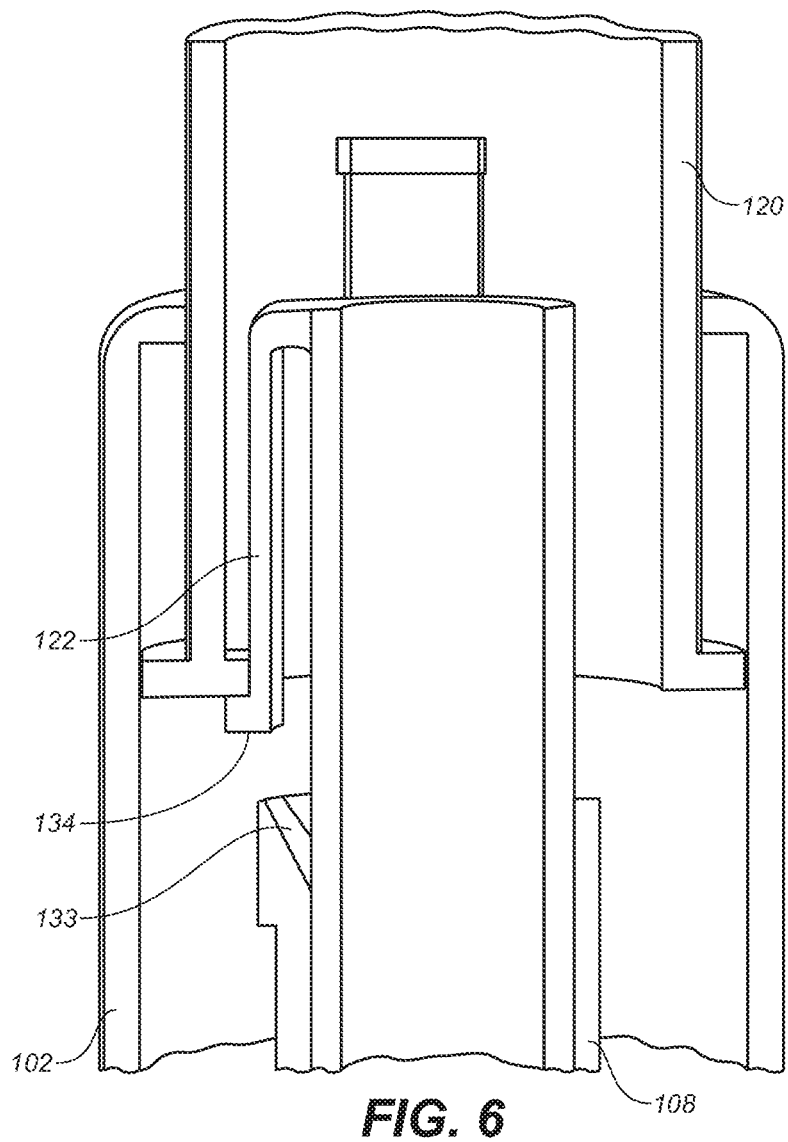
FIG. 6 is a depiction of a partial cross-sectional view of a portion of the embodiment of FIG. 1A, depicting a latch.

After needle 110 has been inserted into the user, the injection process typically begins, as shown in FIGS. 2A through 2C. With reference to FIG. 6, a housing latch 122 that is a part of lower housing 102 is shown in close-up detail and prevents the upper housing 101 from moving with respect to the lower housing 102 in the device's pre-use state (note that some device components have been removed from FIG. 6 for illustration purposes). When needle guard 108 has completed its upward travel, ramped surface 133 on needle guard 108 contacts a ramped portion of surface 134 that forms the end of housing latch 122, causing the housing latch 122 to deflect inwardly, thus allowing the upper housing 101 and upper housing sleeve 120 to move downwardly.

After inserting needle 110 into the body, the user maintains pressure on the upper housing 101. As shown in FIGS. 3, 4, 7 and 8 a plunger rod 115 pushes on a plunger 112. Plunger rod 115 is connected fixedly to the upper housing 101 and syringe 118 is secured to or held in a cylinder formed within lower housing 102. Thus, when the upper housing 101 moves downwardly with respect to and over the lower housing 102, a drug inside the syringe 110 is delivered through the needle 110 to the patient by the downward movement of plunger rod 115 and plunger 112 within syringe 118.

After the housing latch 122 is disengaged, a biasing element 119 that surrounds the distal end of upper housing sleeve 120, is freed from a tensioned state to apply a downward force on the upper housing 101 by exerting a downward force on upper housing sleeve 120, which is fixedly attached, at its uppermost end, to upper housing 101. Biasing element 119 also can be used to provide energy for assisting with advancement of plunger rod 115 and plunger 112 with the user providing additional required force resulting in injection of the drug or the energy supplied by the biasing element 119 may be sufficient only to advance plunger rod 15 and plunger 112. In another embodiment of the present invention, biasing element 119 provides sufficient force to inject the drug, without additional force input required by the user, thus providing an injection device in which the needle is manually inserted and the drug is automatically injected. The biasing element may be any component capable of exerting a downward force on upper housing sleeve 120 to the degree desired and may be, without limitation, a spring, a compressed gas actuator, a hydraulic drive, a wax actuator, an electrochemical actuator, a shape memory alloy, and the like and the combinations thereof. In the embodiment depicted in FIGS. 1 through 9, the user provides the additional force required to advance the plunger rod 115 and plunger 112 by pressing downwardly on the upper housing 101. Thus, the force required by the user to inject the drug is reduced, in a manner analogous to the way power steering in a car reduces the force required by the driver to turn the steering wheel. Unlike conventional auto-injectors, the user contributes to the force required for injection and the present invention provide the user control over the rate of injection of the drug.

Referring to FIGS. 4 and 7, cross sectional views of embodiments of the present invention are shown both before and after delivery of the drug has commenced, respectively. As the drug is being delivered, a pawl 117 which is attached to upper housing sleeve 120 moves along a ratchet 116 that is attached to the lower housing 102. The pawl 117 and the ratchet 116 may serve, at least, the following two functions. First, separation of upper housing 101 from lower housing 102 by pulling them apart is prevented. Second, the motion of pawl 117 along ratchet 116 produces a soft clicking noise, providing feedback to the user that upper housing 101 is moving and the drug is being delivered. Additionally, and as illustrated in FIG. 8, at the end of travel of upper housing 101, pawl 117 may be configured to engage a deeper recess in ratchet 116, thereby producing a louder clicking sound, which can provide an audible signal to the user that end of travel has been reached and the drug has been fully delivered, and further locking the upper housing 101 in place to prevent resetting or reuse of the device.

Figure 8:
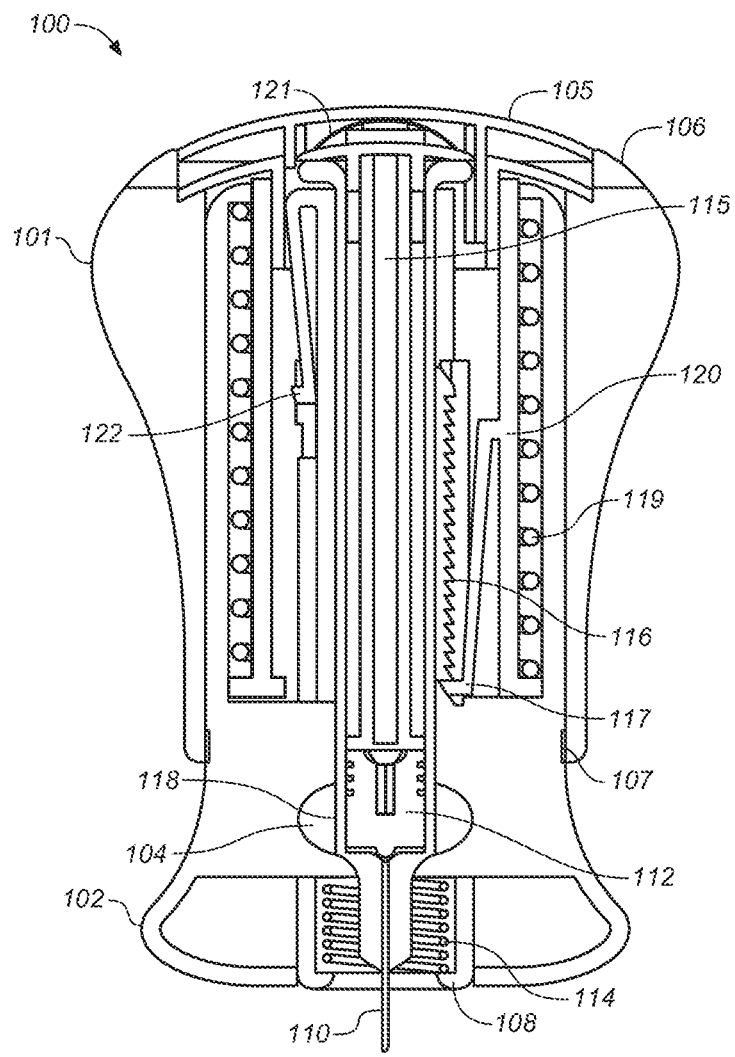
FIG. 8 is a depiction of a cross-sectional view of the embodiment of FIG. 2B.

Referring to FIGS. 2B and 8, when the drug is completely injected and upper housing 101 is at the end of its travel, bottom edge 111 of upper housing 101 covers dose indicator 107. Dose indicator 107 is a circumferential, colored ring at the distal portion of lower housing 102. This provides a visual cue to the user that the drug delivery has been completed.

Prior to use, the patient can view the drug through window 104 to inspect it for clarity and particulates. After use, the plunger 112 can be viewed in the window 104, indicating that the device has been used. Alternatively, the window can be designed such that the plunger rod 115 as well is visible after the injection is complete. The plunger 112 and the plunger rod 115 can be brightly colored to provide a clear indication to the patient that the device has been used.

Figure 9:
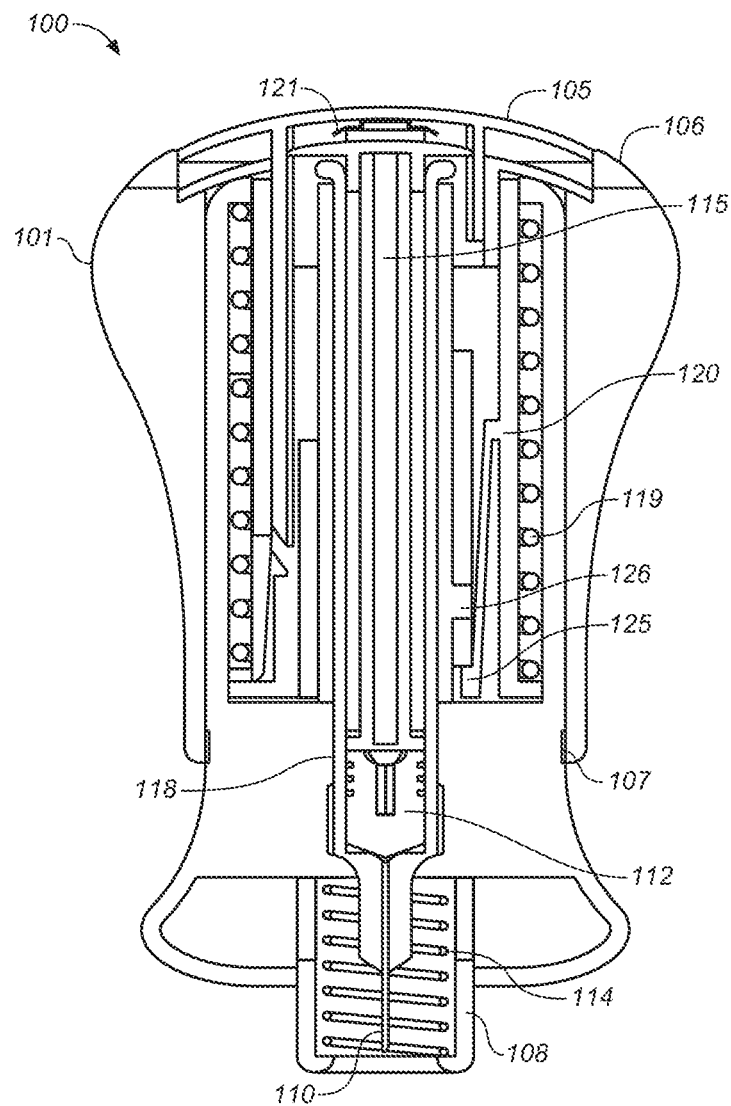
FIG. 9 is a depiction of a cross-sectional view of the embodiment of FIG. 2C

Referring to FIGS. 2C and 9, after completing the injection, the user removes device 100 from the skin, and needle guard return element 114 causes needle guard 108 to extend over needle 110, protecting the user and others from accidental needle punctures. Needle guard return may be any element capable of causing needle guard 108 to extend over needle 110 including, without limitation, a spring, a compressed gas actuator, a hydraulic drive, a wax actuator, an electrochemical actuator, a shape memory alloy, and the like and the combinations thereof. Once needle guard 108 is fully extended, a needle guard lock 125 engages a slot in needle guard 108, preventing the needle guard 108 from retracting. Needle guard lock 125 is a cantilever latch extending inwardly from the inner surface of upper housing sleeve 120. Lower housing rib 126, a part of the lower housing 102, may be configured to prevent the needle guard lock 125 from engaging the slot in the needle guard 108 prematurely during delivery by blocking the slot. In another embodiment of the present invention, needle guard 108 may extend and lock in place if device 100 is removed before delivery is complete, to prevent reuse, or sharing of the device.

With the assisted delivery approach offered by the present invention, the user is actively engaged during the entire delivery process. This is distinguishable from the activation process for conventional auto-inserters, in which after pressing the button, the user passively waits, for several second, for the drug to be delivered, sometimes wondering whether the injection is in process or not.

The assisted activation approach of the present invention has the additional advantage that it reduces development time and cost associated with modifying the injection device for delivering different drugs because the user controls delivery speed by varying the force applied to the upper housing 101. If the plunger is slightly stuck, the user can apply a little more force, unlike conventional auto-injectors that must be designed for worst case force requirements, that vary depending on the drug, cartridge, plunger, needle, and friction in the mechanism.

In another embodiment, the interlock button 105 and the interlock spring 121 can be omitted from the design. In this embodiment, the upper housing 101 is free to move downwardly before hitting a stop. This movement is used to unlock the needle guard 108 using a mechanism similar the interlock mechanism described above, allowing the needle guard 108 to retract. Once the needle guard 108 is fully retracted, it may disengage another latch that allows the upper housing 101 to discontinue moving downwardly and inject the drug in a similar manner as is described above.

In FIGS. 10 through 18 is depicted yet another embodiment of the invention. In FIG. 10A is shown device 200 with upper housing 205, lower housing 202 and middle housing 201 therebetween. Upper housing 205 includes grip cap 228. In the relaxed position, upper housing 205 partially overlies the proximal, portion of middle housing 201. The distalmost portion of middle housing 201 is fixedly seated in lower housing 202. Also shown in FIG. 10A are upper housing bottom edge 211, travel ridge 216, and window 204. Window 204 preferably is seated within the proximal portion of lower housing 202. A second window, not shown, preferably is present on the device on the side opposite of window 204.

Figure 10A:
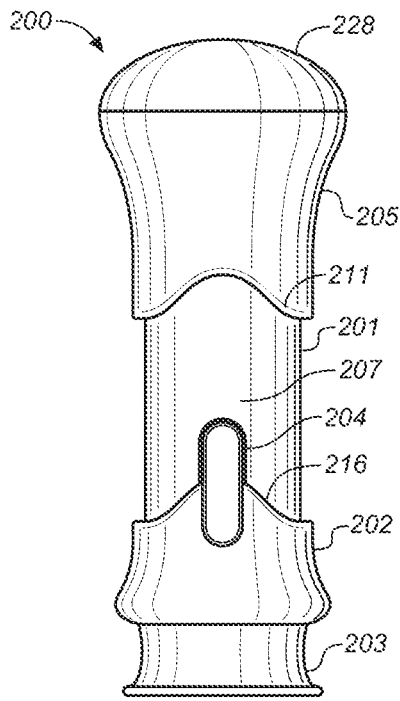
FIG. 10A is a side view of another embodiment of the present invention.
Figure 10B:
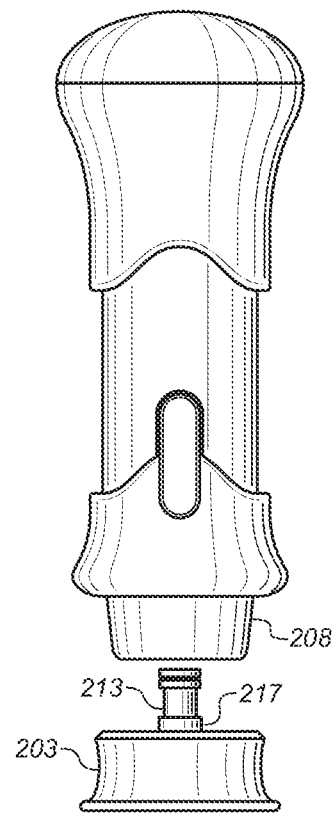
FIG. 10B is a side view of the embodiment of FIG. 10A after cap removal.
Figure 10C:
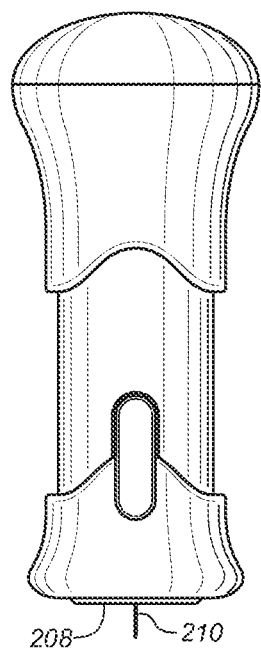
FIG. 10C is a side view of the embodiment of FIG. 10B after the needle guard has been retracted, exposing the needle.

Cap 203 is removably attached to lower housing 202 and, in FIG. 10B, is shown removed from device 200 to expose needle shield 213, needle shield clamp 217 and needle guard 208. During removal of cap 203, needle shield clamp 217 grabs and simultaneously removes needle shield 213 exposing needle guard 208 to the user. When the device user presses the needle guard 208 against the skin, this action causes needle guard 208 to slide upwardly exposing needle 210, as shown in FIG. 10C.

Figure 12:
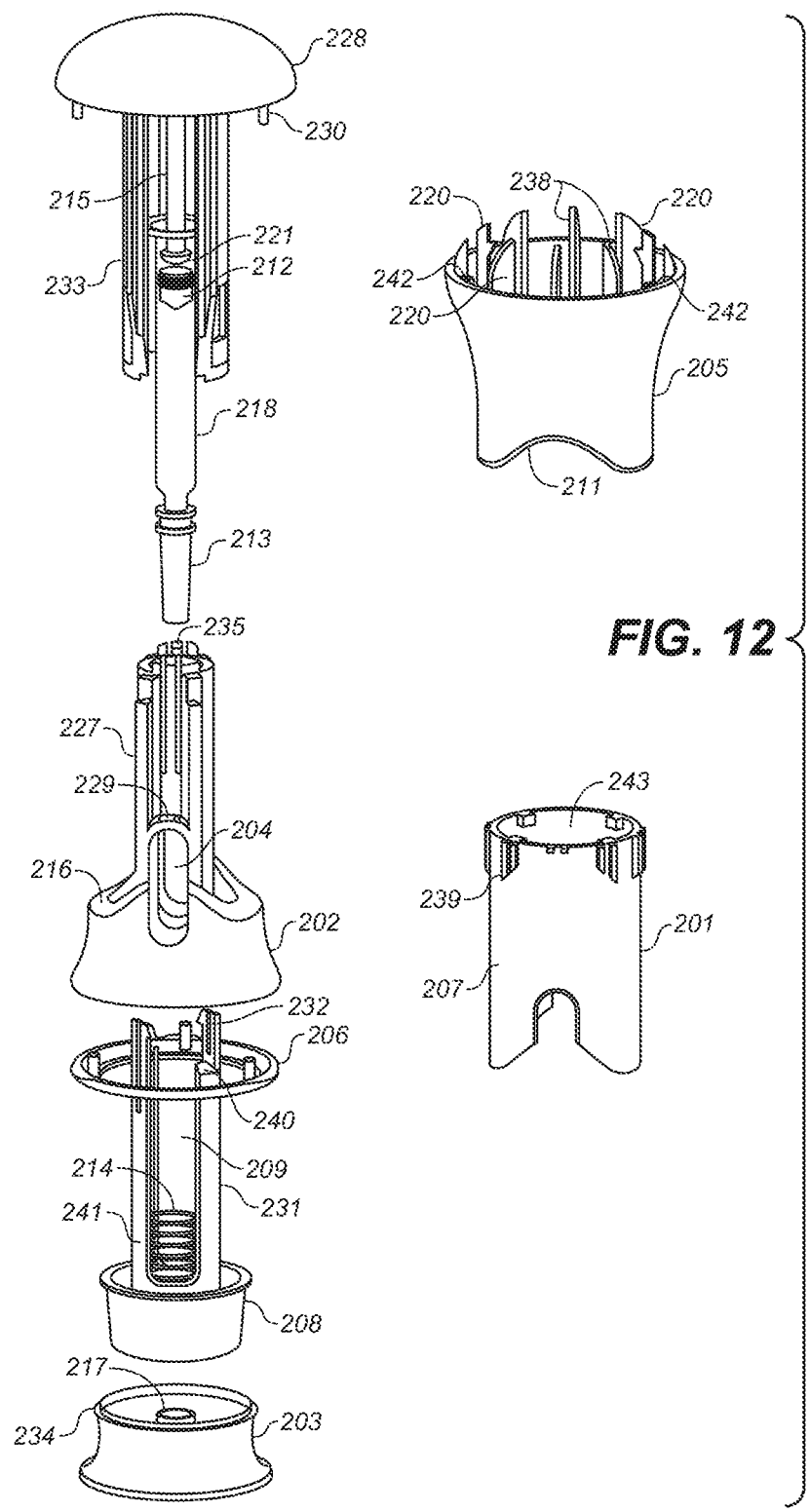
FIG. 12 is a depiction of an exploded view of the embodiment of FIG. 10A.

FIG. 12 is an exploded view of device 200. Grip cap 228 includes grip cap assembly pins 230 that fixedly secure grip cap 228 on upper housing 205. Assembly pins 230 mate with holes 242 in upper housing 205. Preferably, assembly pins 230 are square in cross-section with rounded corners providing an interfering surface between the corners of assembly pins 230 and holes 242. Guides 233 and plunger rod 215, which are integral with and extend downwardly from the inner surface of grip cap 228 as shown. Plunger rod 215 includes a damper 221 at its distal end. Also shown are syringe 218 with plunger 212 and needle shield 213.

In a preferred embodiment, the external surface of grip cap 228 is coated with or formed from, or the entirety of grip cap 228 is formed from, a material capable of providing a soft, non-slip grip for the user. Suitable materials for coating or forming the grip cap include, without limitation, elastomeric materials such as neoprene rubber, urethane, polyurethane, silicone, natural rubber, TPE and the like and combinations thereof.

Upper housing 205 includes click latch 220, handle rib guide 238, and bottom edge 211. For click latch 220, as well as the other latches used in the device, preferably at least two latches are used and the same latches are symmetrically positioned with respect to each other to facilitate smooth movement and operation of the device.

Middle housing 201 is shown in FIG. 12 with body 207 and handle guide slots 239 on the external surface of the proximal portion of body 207. When the device is in use, handle rib guides 238, which are an integral part of upper housing 205, engage with and slide within handle guide slots 239, maintaining smooth and controlled motion of upper housing 205 during drug delivery.

Body 207 may serve as a dose indicator because, as the device is activated, upper housing 205 descends over body 207. When the complete medication dose has been delivered, body 207 is fully obscured by upper housing 205 as shown in FIG. 11C. Preferably body 207 is colored, more preferably with a bright color, or is patterned to provide easily viewed visual feedback to the user that the dosing is progressing or has been completed. Optionally, a scale may be included on body 207 to visually quantify the amount of drug that has been delivered or remains to be delivered.

Figure 13A:
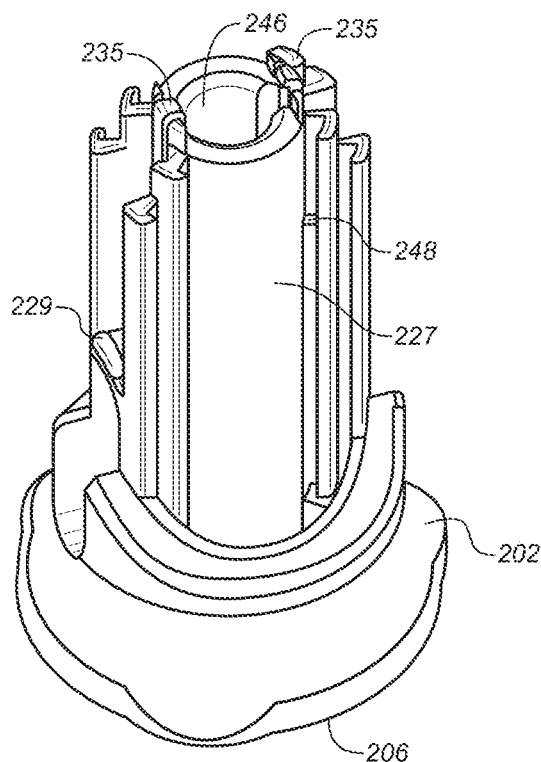
FIG. 13A is a perspective view of the lower housing of the embodiment of FIG. 10A.
Figure 13B:
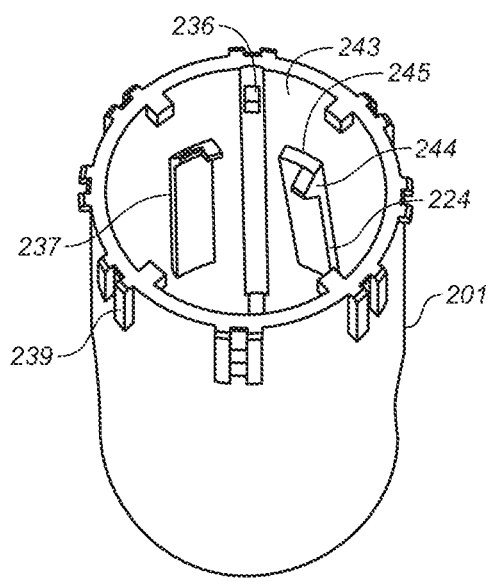
FIG. 13B is a perspective view of the middle housing of the embodiment of FIG. 10A.

With reference to FIG. 13, middle housing 201 also includes grip latches 224, click latch capture slots 236, and needle guard latch 237. Grip latch 224 is a generally rectangular element movably attached at its distal-most portion to the inner surface 243 of middle housing 201 so that it is capable of movement outwardly toward inner surface 243 upon application of force. Grip latch 224 also includes a stop surface 245 and a triangular shaped stop 244 extending inwardly toward the device's center from one corner of its topmost portion. In the device's resting, pre-use position grip latch 224 prevents upper housing 205 from moving with respect to middle housing 201 due to stop 245 interfering with the downward travel of guides 233 of grip cap 228.

With reference to FIGS. 12 and 13, lower housing 202 is shown with lower housing base 206, end of travel ridge 216, window 204, housing latch 229, guide slots 227 and syringe retainer clip 235. Cap 203 removably attaches to lower housing base 206 via cap retainer ring 234. In use, lower housing base 206 contacts the user's skin and, thus, preferably is made of any of the soft flexible materials suitable for use for grip cap 228.

Window 204 provides an opening in lower housing 202 for viewing of the contents of syringe 218. Window 204 is positioned such that the bottom of syringe 218 is visible to the user allowing the user to verify that plunger 212 has reached the end of its travel to the bottom of the syringe. Window 204 may be any convenient size and shape and preferably is oblong in shape with its long axis aligned with the long axis of the device and syringe so that the desired length of the syringe is exposed to view.

Guide slots 227 maintain the alignment of three different components: guides 233 of grip cap 228; grip latch release 231; and needle guard extensions 241. Guide slots 227 ensure smooth activation of the device by maintaining alignment and vertical travel of upper housing 202 and needle guard 208 and reliable latching and unlatching of grip latch 231. Housing latch 229 extending outwardly secures middle housing 201 to lower housing 202 by engaging a recess, that is not shown, in inner surface 243 of middle housing 201. In non-reusable embodiments of the device, the shape of latch 229 and the recess are such that the middle and lower housing cannot be separated. For reusable embodiments, the recess and latch are configured to enable the middle and lower housing to be pulled apart.

Figure 14:
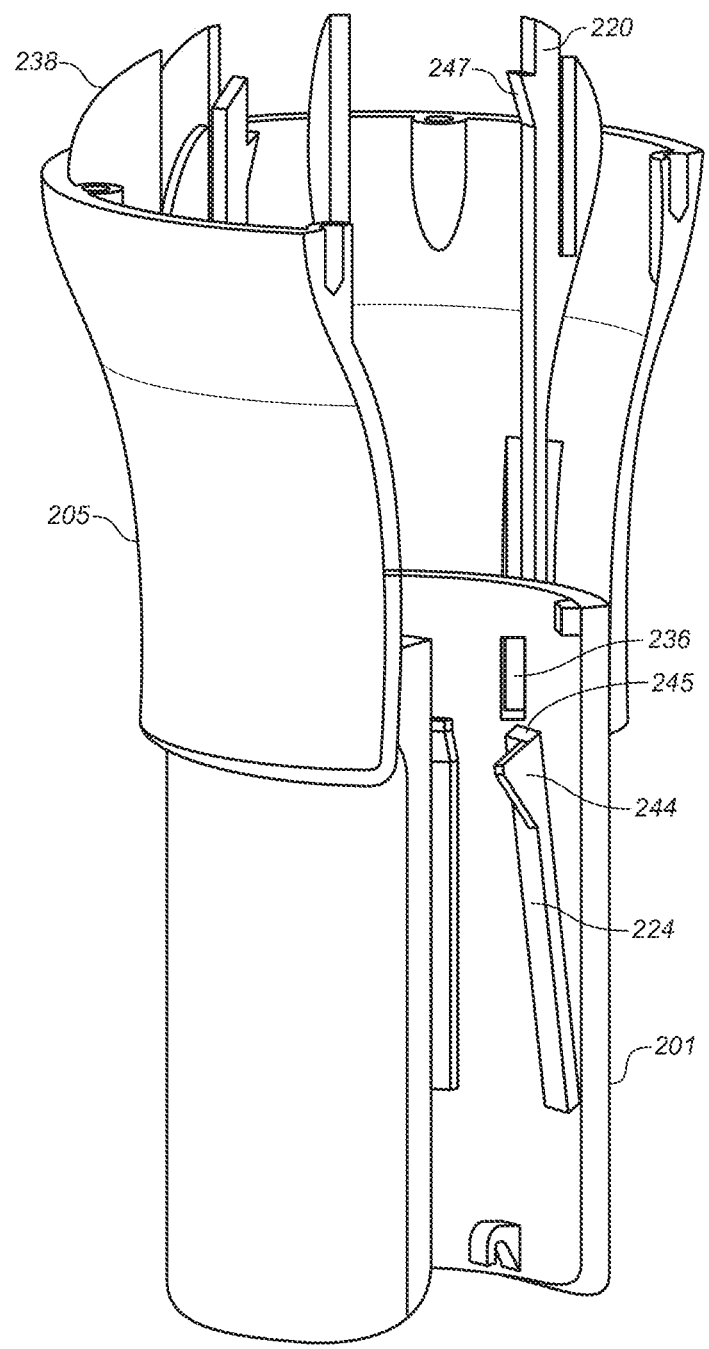
FIG. 14 is a depiction of a partial cross-sectional view of a portion of the upper and middle housings of the embodiment of FIG. 10A.
Figure 15:
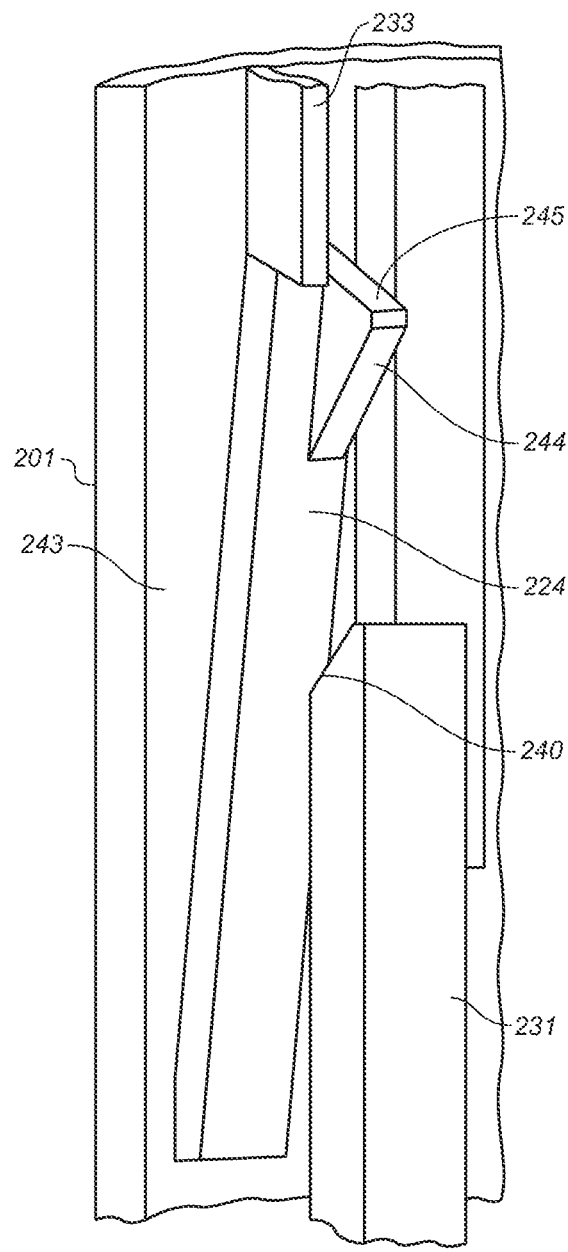
FIG. 15 is a depiction of a latching mechanism of the embodiment of FIG. 10A

Referring to FIG. 12, needle guard 208 includes needle guard slot 209 formed on one side by grip latch release 231 and the other side by needle guard extension 241. Grip latch release 231 includes ramped surface 240. Referring to FIGS. 14 and 15, ramped surface 240 of grip latch release 231 faces outwardly and, as grip latch 231 travels upwardly, engages ramped surface 244 of grip latch 224, which faces inwardly, causing grip latch 224 to deflect outwardly, removing the obstruction to the downward movement of guide 233 and 205.

Needle guard slot 209 permits window 204 to be used to view the syringe and plunger as the plunger acts on the syringe at the end of the plunger's downward stroke. Additionally, needle guard return 214 lies within and at the bottom of a space formed by grip latch release 231 and needle guard extension 241.

Figures 17A, 17B:
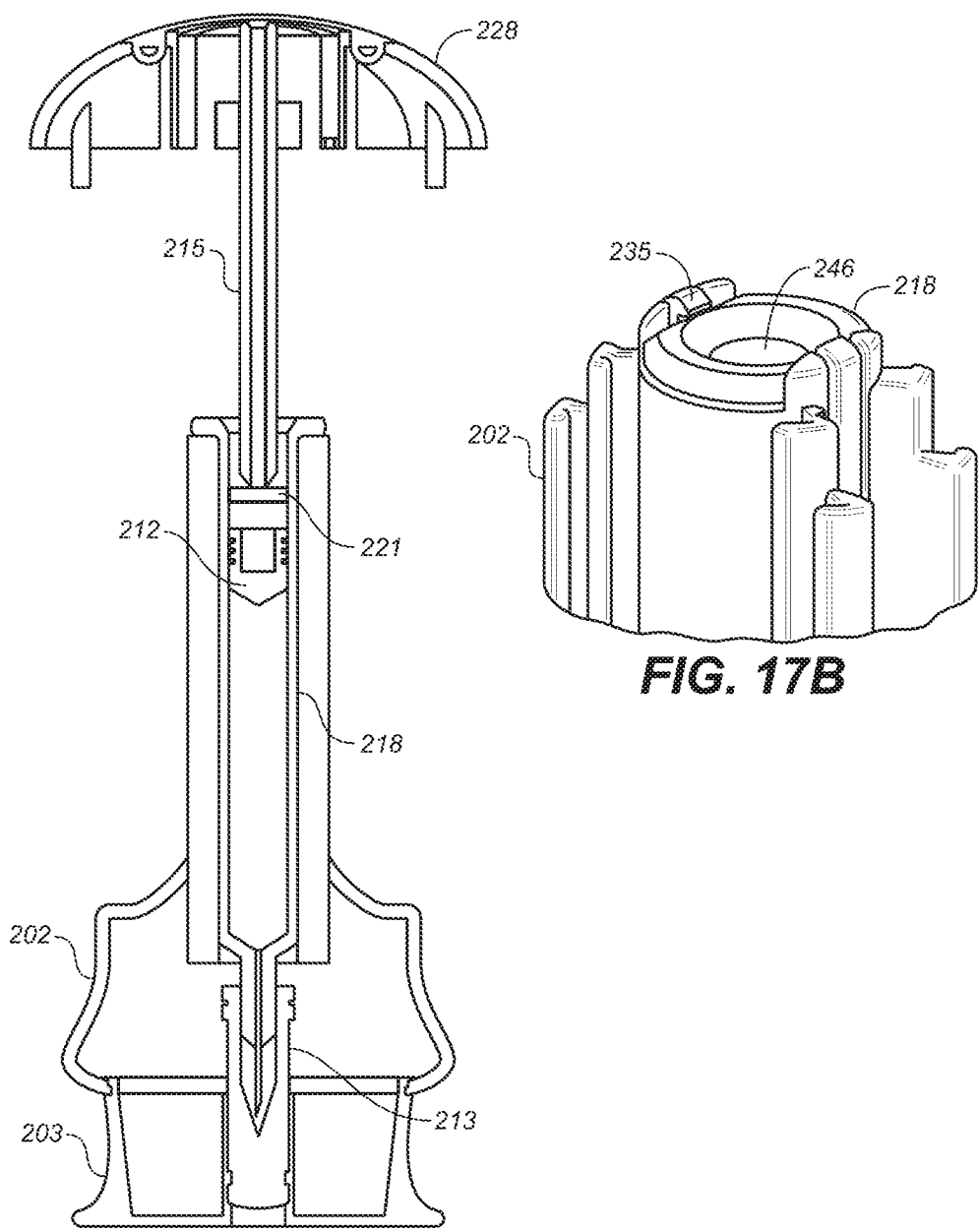
FIG. 17A is a depiction of a cross-sectional view of a portion of the embodiment of FIG. 10A.
FIG. 17B is a depiction of a perspective view of a portion of the lower housing of the embodiment of FIG. 10A.
Figure 18:
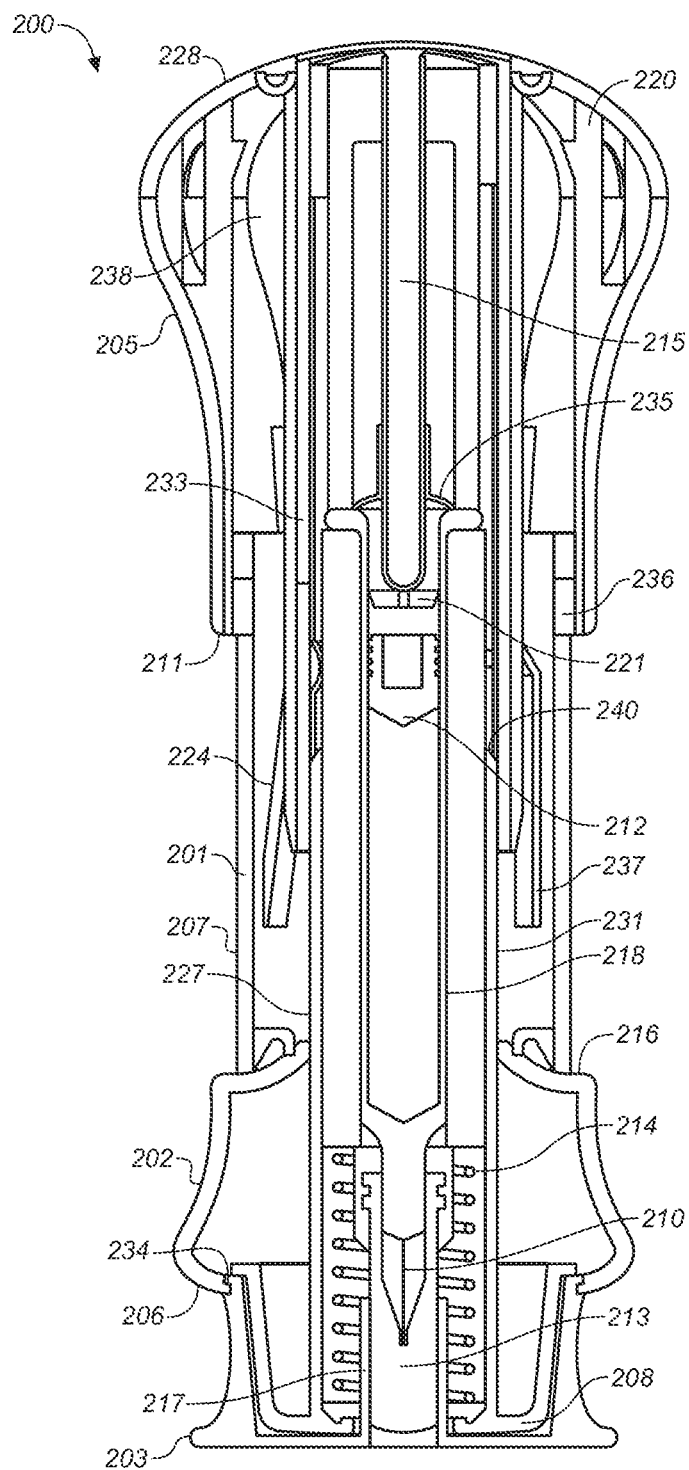
FIG. 18 is a cross-sectional view of the device of FIG. 10A.

An inventive aspect of the device 200 is the way in which syringe 218 is suspended inside the device. With reference to FIGS. 12, 13, and 17, syringe 218 is held between needle shield 213 and damper 221, each of which are flexible components, to protect syringe 218 in the event device 200 is dropped or otherwise mishandled. When the device is assembled, syringe 218 is loosely held within cavity 246 of lower housing 202 by retainer clips 235. Depending on the volume of medication within syringe 218, when the device is in used, there may be some travel of upper housing 205 before damper 221 contacts plunger 212 and, during this initial downward travel, damper 221 acts as an air piston to compress the air in the gap formed between the end of plunger rod 215 and plunger 212, which provides a rate-dependent resistance to motion to the initial downward motion of grip. When damper 221 moves fast, air cannot escape quickly enough to reduce the build-up of air pressure. Damper 221 may optionally include through-holes, that are not shown, therein to allow air to leak past damper 221. Alternatively, a friction-based resistance from the damper without pressure build-up, use a damper in which there is no leak and no rate dependence, or combinations thereof may be used. Upon contact of damper 221 with plunger 212, damper 221 collapses inwardly towards plunger rod 215 reducing the friction between damper 221 and the inside surface of cavity 246.

Figure 11A:
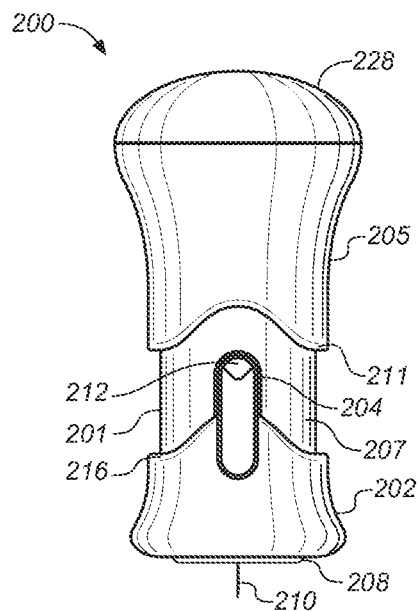
FIG. 11A is a side view of the embodiment of FIG. 10C during drug injection.
Figure 11B:
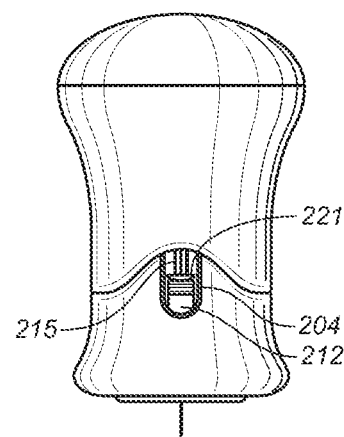
FIG. 11B is a side view of the embodiment of FIG. 11A upon completion of drug injection.
Figure 11C:
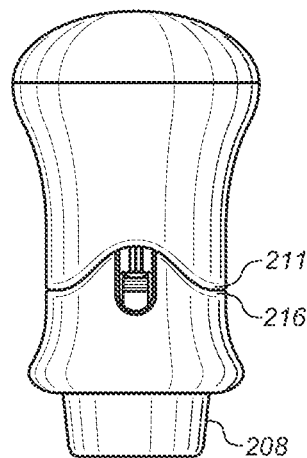
FIG. 11C is a side view of the embodiment of FIG. 11B after the needle guard has been extended, concealing the needle.

With reference to FIGS. 10 and 11, when the user desires to use device 200, the user removes cap 203 from lower housing 202, which action simultaneously removes needle shield 213 and exposes needle guard 208. The user grasps device 200 by upper housing 205, places the palm of the hand over grip cap 228 and presses downwardly on grip cap 228 while holding the device 200 against the desired injection site on the body, which pressing action causes needle guard 208 to slide upwardly exposing needle 210. Continuing application of pressure to grip cap 228 results in needle 210 penetrating the user's skin and sub-dermal tissue, stopping when lower housing base 206 contacts the skin surface or when the rim 245 reaches of needle guard 208 reaches the end of its travel within lower housing 202.

With reference to FIG. 15, when needle guard 208 reaches the end of its upward travel within lower housing 202, ramped surface 240 of grip latch release 231 contacts the oppositely facing and complementarily ramped surface 244 of grip latch 224 of middle housing 201 causing grip latch 224 to deflect towards the inner wall 243 of middle housing 201. This action removes stop surface 245 of grip latch 224 from interfering with the downward travel of guide 233 of grip cap 228 freeing guide 233 and allowing upper housing 205 to move downwardly and over middle housing 201.

When upper housing 205 moves downwardly, the medication inside of syringe 218 is delivered through needle 210 as plunger rod 215 and damper 221 of grip cap 228 push downwardly on syringe plunger 212. At the end of the medication delivery, body 207 is substantially completely covered by upper housing 205 and bottom edge 211 of upper housing 205 has mated with the complementarily shaped travel ridge 216 of lower housing 202. Also, plunger rod 215, damper 221, and plunger 212 are clearly visible within window 204. All of these features provide the user with visual confirmation that the drug has been delivered and the hard stop of bottom edge 211 against travel ridge 216 provides a tactile confirmation to the user.

Additionally, a click mechanism is activated at the end of drug delivery to provide audible feedback. With reference to FIG. 14, click latch 220 is deflected outwardly when ramp 247 thereof contacts and slides past the top of middle housing 201. When the ramp 247 moves sufficiently far downwardly, ramp 247 aligns with click latch capture slot 236 and the ramp 247 slips into capture slot 236, which slot extends through the wall at the proximal portion of middle housing 201, and snaps against the outer surface of body 207 of middle housing 201 creating a clicking sound. In non-reusable versions of the device, click latch 220 is permanently captured by capture slot 236 and cannot be reset. In a preferred embodiment, two click latches 220 are positioned at positions 180 degrees opposite of each other in order to provide smooth activation of the device and to enhance the clicking and latching functions.

Figure 16:
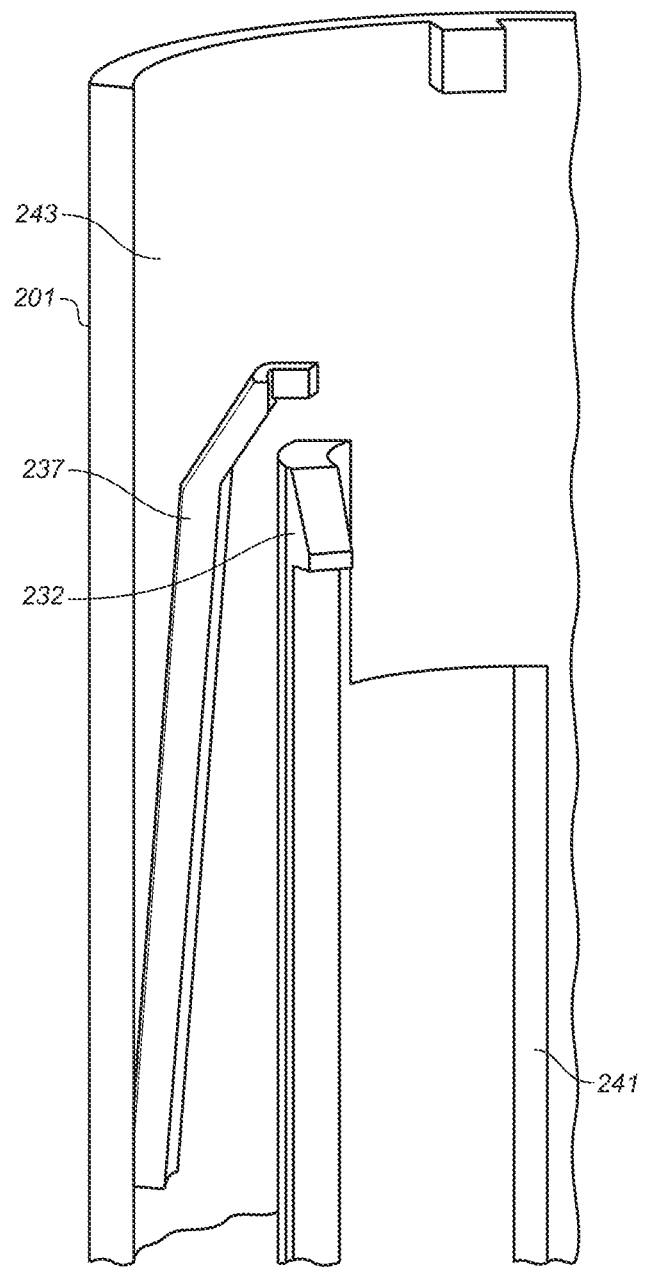
FIG. 16 is a depiction of another latching mechanism of the embodiment of FIG. 10A.

As the user removes device 200 from the skin, needle guard return 214, shown in FIG. 12 as a spring, that was compressed by pressing of device 200 against the user's skin, expands causing needle guard 208 to extend downwardly over needle 210 protecting the user from accidental punctures. In addition to a spring, the needle guard return may be a compressed gas actuator, a hydraulic drive, a wax actuator, an electrochemical actuator, a shape memory alloy, and the like and the combinations thereof. When needle guard 208 is fully extended, needle guard retainer 232 engages stop 248, shown in FIG. 13, on lower housing 202 preventing needle guard 208 from separating from lower housing 202. In FIG. 16 is shown needle guard latch 237 movably attached at its distal end to the inner surface 243 of middle housing 201. When needle guard 208 is upwardly traveling, needle guard latch 237 is deflected outwardly on contact with the outer surface of guide 233 or of needle guard extension 241. When needle guard 208 travels downwardly and extends to cover needle 210, needle guard latch 237 slips over the top of needle guard extension 241 preventing needle guard 208 from again retracting.

Prior to use, extension guides 233 of grip cap 228 retain needle guard latch 237 in an outwardly deflected position allowing needle guard 208 to retract for insertion of needle 210. Two needle guard retainers 232 and needle guard latches 237 preferably are used and are located 180 degrees apart around the central axis of the device 200. If the device 200 is removed from the skin before delivery of medication is completed, needle guard 208 will extend to cover needle 210 and locks to prevent reuse of the device. In an alternative, reusable embodiment, needle guard 208 extends, but does not lock in place in the event device 200 is removed from the skin before delivery of medication is completed.

Figure 19:
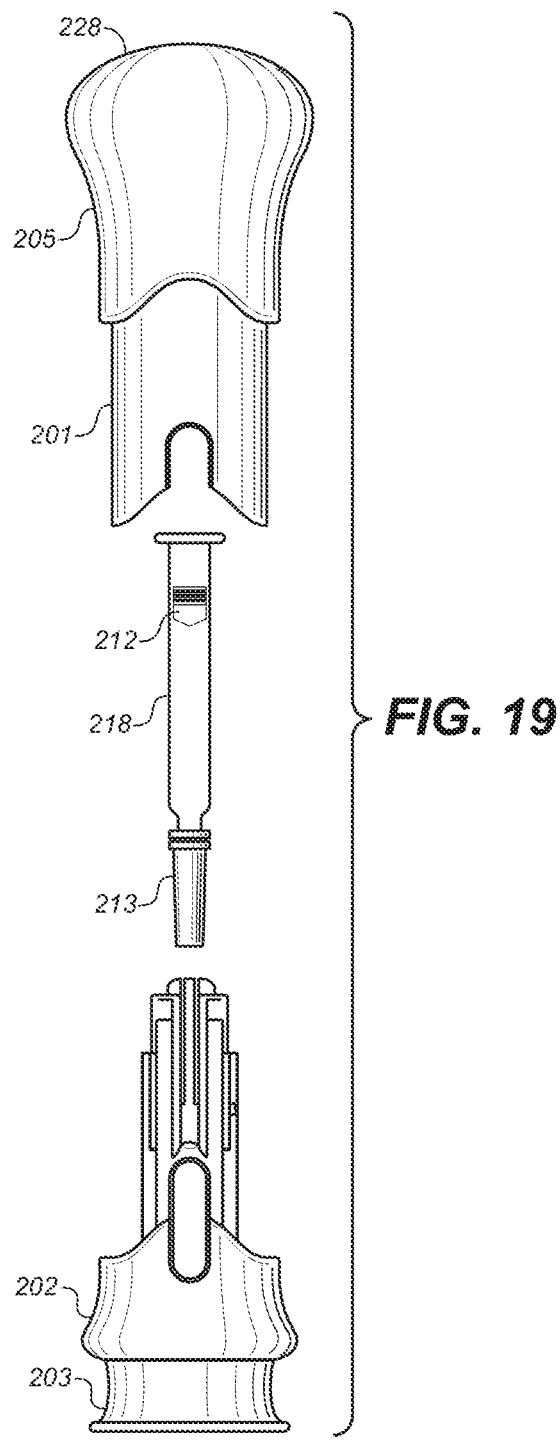
FIG. 19 is an exploded, side view of still another embodiment of the present invention.

FIG. 19 is a depiction of an alternative, reusable embodiment of device 200 in which upper housing 205 and middle housing 201 are separable from lower housing 202. In this embodiment, the user separates the middle and lower housings, inserts syringe 218 into the lower housing and then reattaches the middle and upper housings.

Figure 20:
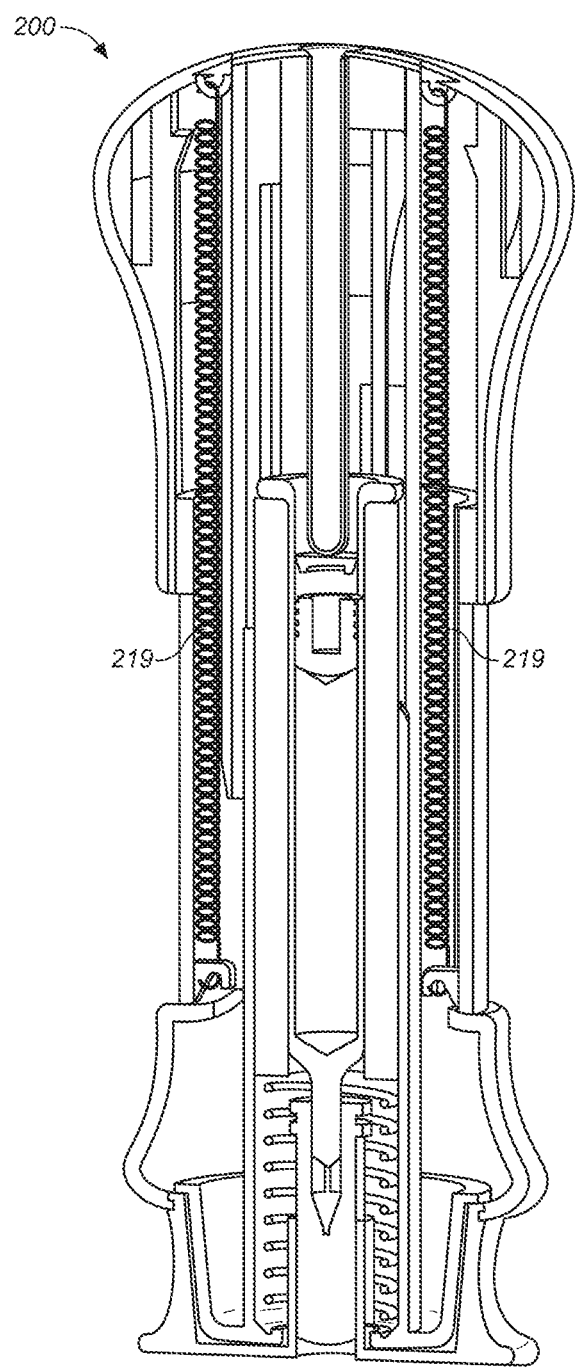
FIG. 20 is a depiction of a cross-sectional, side view of yet another embodiment of the present invention prior to use.

In FIG. 20 is depicted yet another alternative embodiment of device 200 in which an assist drive 219 is included. Assist drive 219 may find its greatest utility in delivering viscous drugs. The assist drive 219 applies a force between upper housing 205 and middle housing 201 exerting a downward force on upper housing sleeve 120. This reduces the amount of downward force the user must apply to grip cap 228 in order to inject the drug. Assist drive 219 may be a spring, a compressed actuator, a hydraulic drive, a wax actuator, an electrochemical actuator, a shape memory alloy or the like or combinations thereof. Alternatively, assist drive may provide sufficient force to inject the drug, without additional force input required by the user, thus providing an injection device in which the needle is manually inserted and the drug is automatically injected in a manner similar to a conventional auto-injector.

Figure 21A:
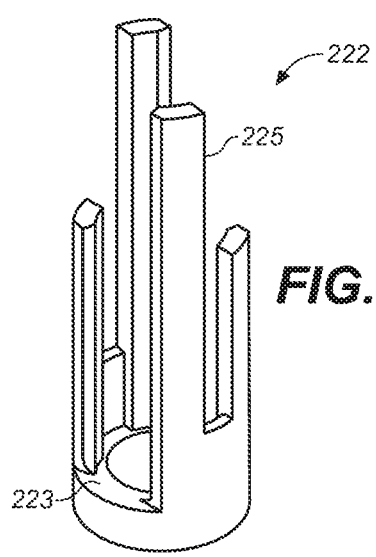
FIG. 21A is a perspective view of an alternative design of the lower housing of the embodiment of FIG. 10A.
Figure 21C:
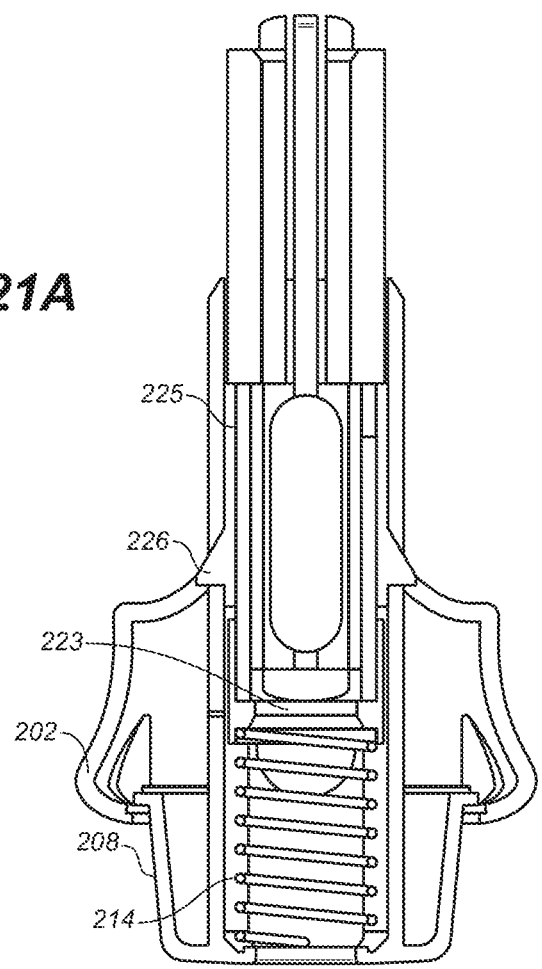
FIG. 21C is a cross-sectional view of the lower housing of FIG. 21B.
Figure 21B:
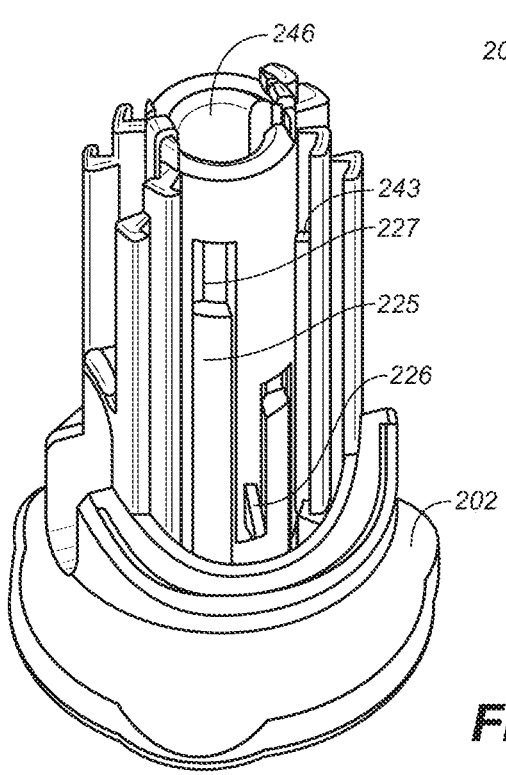
FIG. 21B is a perspective view of an alternative embodiment of the lower housing of FIG. 10A.

In FIG. 21 is depicted an alternative embodiment of lower housing 202 of device 200 in which a resettable clicking mechanism for a reusable device is included. In this embodiment, guide slots 227 engage guide 2225 of clicker 222. Clicking device 222 is biased by needle guard return 214. To set clicking device 222, the user presses down on one of clicker guides 225 until clicker latch 226 extends over clicking device 222 holding it down. When grip cap 228 moves downwardly, at the end of travel, guide 233 contacts a ramped surface on clicker latch 226 causing it to deflect inwardly and releasing clicker 222 to travel upwardly under the force of needle guard return 214. A click sound is generated when click surface 223 of clicker 222 contacts lower housing 202 signaling that the drug has been completely delivered. The compressing of needle guard return 214 is increased when needle guard 208 is retracted during injection of the drug, increasing the force applied to the clicking device and the volume of the click sound. Alternatively, the click mechanism can be reset automatically when the user attaches the upper housing to the lower housing upon loading a new syringe into the device.

Additional embodiments of the present invention can be envisioned, but are not included in the attached figures. This includes a multiple-dose design in which one or both of the upper and middle housings rise to a partial height and deliver a partial syringe when depressed by the user.

What is claimed is:

1. A method of injecting a medication from a medication delivery device of the type including an upper housing, a lower housing, a syringe supported by the lower housing and having a needle, and a needle guard supported by the lower housing, the method comprising the steps of:
   placing the medication delivery device against a skin surface so as to cause the needle guard to abut the skin surface, wherein the upper housing is releasably locked with respect to movement toward the needle;
   applying a force against the upper housing along an insertion direction, thereby causing the skin surface to force the needle guard to retract relative to the lower housing and thereby expose the needle so as to insert the needle through the skin surface, wherein the applying step causes the needle guard to unlock the upper housing with respect to movement toward the needle, thereby allowing movement of the upper housing toward the needle; and
   after the unlocking step, continuing to apply the force against the upper housing along the insertion direction, thereby causing the upper housing to move toward the needle, thereby driving a medication contained within the syringe out the needle.

2. The method of claim 1, wherein the continuing step further comprising the step of driving a plunger rod into the syringe so as to drive the medication out the needle.

3. The method of claim 1, wherein the medication delivery device includes a latch that interferes with the upper housing so as to releasably lock the upper housing with respect to movement toward the needle, and the unlocking step comprises causing the needle guard to contact the latch and bias the latch away from the upper housing to thereby unlock the upper housing.

4. The method of claim 1, further comprising moving the medication delivery device away from the skin surface along a direction opposite the insertion direction so as to remove the needle from the skin surface.

5. The method of claim 4, wherein the moving step further comprises causing the needle guard to advance relative to the needle so as to substantially encapsulate the needle.

6. The method of claim 5, wherein the moving step further comprises preventing the needle guard from retracting with respect to the needle.

7. The method of claim 1, further comprising the step of, after the continuing step, preventing the upper housing from retracting away from the needle.

8. The method of claim 1, wherein the upper housing is unlocked with respect to movement toward the needle as the needle guard completes its travel relative to the lower housing.

9. The method of claim 1, wherein the medication delivery device further includes a middle housing coupled between the upper housing and the lower housing.

10. A method of injecting a medication from a medication delivery device of the type including an upper housing, a lower housing, a syringe supported by the lower housing and having a needle, a needle guard supported by the lower housing, and a middle housing coupled between the upper housing and the lower housing, the method comprising the steps of:
    placing the medication delivery device against a skin surface so as to cause the needle guard to abut the skin surface, wherein the upper housing is releasably locked with respect to movement toward the needle;
    applying a force against the upper housing along an insertion direction, thereby causing the skin surface to force the needle guard to retract relative to the lower housing and thereby expose the needle so as to insert the needle through the skin surface;
    during the applying step, unlocking the upper housing with respect to movement toward the needle, thereby allowing movement of the upper housing toward the needle; and
    after the unlocking step, continuing to apply the force against the upper housing along the insertion direction, thereby causing the upper housing to move toward the needle, thereby driving a medication contained within the syringe out the needle.

11. The method of claim 10, wherein the continuing step comprises the step of progressively covering a body of the middle housing with the upper housing to thereby provide a visual indication that the medication is being delivered.

12. The method of claim 11, wherein the progressively covering step further comprises substantially completely covering the middle housing with the upper housing so as to indicate that the medication has been fully delivered.

13. The method of claim 10, wherein the continuing step further comprising the step of driving a plunger rod into the syringe so as to drive the medication out the needle.

14. The method of claim 10, wherein the medication delivery device includes a latch that interferes with the upper housing so as to releasably lock the upper housing with respect to movement toward the needle, and the unlocking step comprises causing the needle guard to contact the latch and bias the latch away from the upper housing to thereby unlock the upper housing.

15. The method of claim 10, further comprising moving the medication delivery device away from the skin surface along a direction opposite the insertion direction so as to remove the needle from the skin surface.

16. A method of injecting a medication from a medication delivery device of the type including an upper housing, a lower housing, a middle housing that includes a body that is exposed between the upper housing and the lower housing, and a syringe supported by the lower housing and having a needle, the method comprising the steps of:
    placing the medication delivery device against a skin surface;
    moving the medication delivery device toward the skin surface along a direction to thereby cause the needle to penetrate the skin surface; and
    applying a force to the upper housing along the direction to thereby move the upper housing along the middle housing body toward the needle such that the upper housing progressively covers the middle housing body as the upper housing moves toward the needle to thereby provide a visual indication that medication contained in the syringe is being delivered.

17. The method of claim 16, wherein the applying step comprises moving the upper housing along the middle housing body until a first surface of the lower housing mates with a complimentary second surface at a distal end of the upper housing.

18. The method of claim 17, further comprising causing a tactile feedback when the first surface mates with the corresponding second surface.

19. The method of claim 16, wherein the placing step comprises placing the medication delivery device against a skin surface so as to cause the needle guard to abut the skin surface, wherein the upper housing is releasably locked with respect to movement toward the needle.

20. The method of claim 19, wherein the moving step comprises applying a force against the upper housing along the direction to thereby cause the skin surface to force a needle guard supported by the lower housing to retract relative to the lower housing and expose the needle so as to insert the needle through the skin surface.

\* \* \* \* \*